(12) United States Patent
Banju

(10) Patent No.: US 8,308,633 B2
(45) Date of Patent: Nov. 13, 2012

(54) MANIPULATOR OPERATION SYSTEM

(75) Inventor: Kazuo Banju, Hachioji (JP)

(73) Assignee: Olympus Medical Systems Corp. (JP)

( * ) Notice: Subject to any disclaimer, the term of this patent is extended or adjusted under 35 U.S.C. 154(b) by 1058 days.

(21) Appl. No.: 12/255,049

(22) Filed: Oct. 21, 2008

(65) Prior Publication Data

US 2009/0216077 A1 Aug. 27, 2009

(30) Foreign Application Priority Data

Feb. 21, 2008 (JP) ................................. 2008-040527

(51) Int. Cl.
*A61B 1/00* (2006.01)
*A61B 1/04* (2006.01)
(52) U.S. Cl. ........ 600/118; 600/103; 600/104; 600/117; 600/145; 600/146
(58) Field of Classification Search .................. 600/103, 600/104, 117–118, 145–146
See application file for complete search history.

(56) References Cited

U.S. PATENT DOCUMENTS

| | | | | |
|---|---|---|---|---|
| 5,572,999 | A * | 11/1996 | Funda et al. | 600/118 |
| 5,749,362 | A * | 5/1998 | Funda et al. | 600/407 |
| 5,818,527 | A | 10/1998 | Yamaguchi et al. | |
| 6,402,685 | B1 * | 6/2002 | Igarashi | 600/111 |
| 7,841,980 | B2 * | 11/2010 | Minosawa et al. | 600/118 |
| 2001/0016680 | A1 * | 8/2001 | Minami et al. | 600/167 |
| 2002/0010384 | A1 * | 1/2002 | Shahidi et al. | 600/118 |
| 2004/0127785 | A1 * | 7/2004 | Davidson et al. | 600/407 |
| 2008/0097156 | A1 * | 4/2008 | Nakamura | 600/117 |
| 2009/0097725 | A1 * | 4/2009 | Krupnik et al. | 382/128 |

FOREIGN PATENT DOCUMENTS

| | | |
|---|---|---|
| EP | 1 772 095 A | 4/2007 |
| JP | 8-11071 | 1/1996 |
| JP | 8-187246 | 7/1996 |
| JP | 8-309680 | 11/1996 |
| JP | 2004-041778 A | 2/2004 |

OTHER PUBLICATIONS

European Search Report dated Mar. 16, 2009 in counterpart European Patent Application No. 08018654.7-1265 (English language).

* cited by examiner

*Primary Examiner* — John P Leubecker
*Assistant Examiner* — Arnaldo Torres Diaz
(74) *Attorney, Agent, or Firm* — Ostrolenk Faber LLP

(57) ABSTRACT

A manipulator operation system includes a treatment instrument distal end movement control section having an endoscope treatment instrument having a bending portion and a distal end portion, a bending driving section and a bending operating section. The manipulator operation system includes imaging mechanism having an imaging section that includes an optical system having a field curvature, images, observing mechanism having a display section that displays a taken image, detecting mechanism having a detecting section that detects an arrangement position of the distal end portion, field curvature information acquiring mechanism having a field curvature information acquiring section that acquires field curvature information of the taken image, and adjusting mechanism having an adjustment section that adjusts a ratio of an operation amount of the bending operating section and a driving amount of the bending driving section based on the arrangement position and the field curvature information.

18 Claims, 14 Drawing Sheets

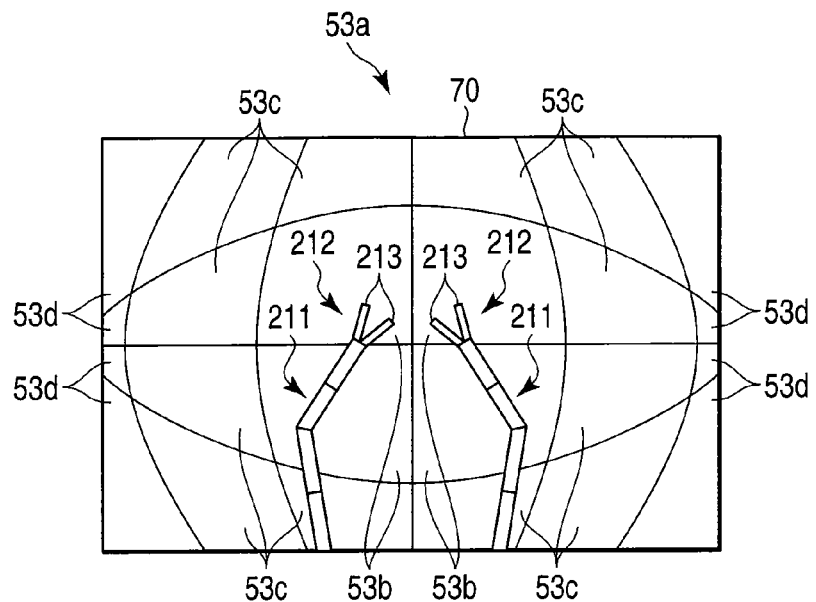
Operation amount: bending amount = 1:1
F I G. 8 A
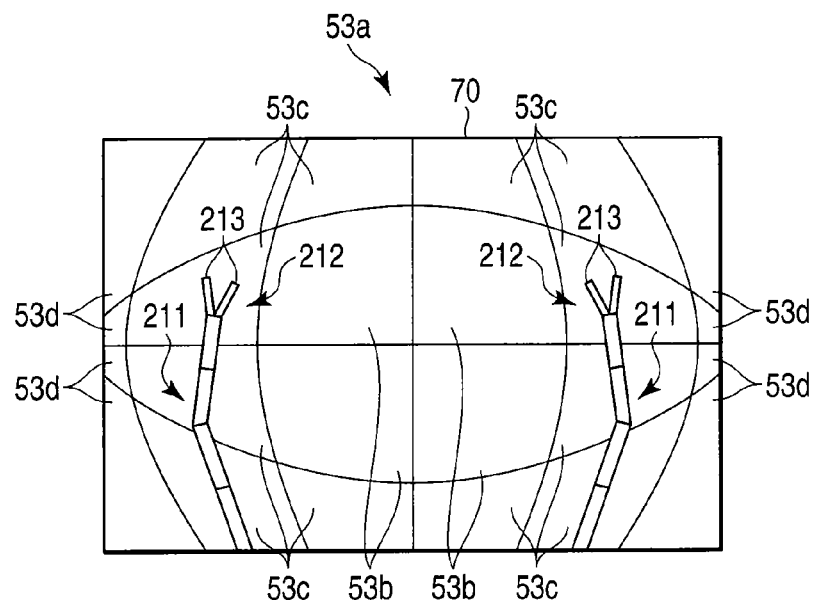
Operation amount: bending amount =1:1/3
F I G. 8 B Operation amount: bending amount = 1:1/5

MANIPULATOR OPERATION SYSTEM

CROSS-REFERENCE TO RELATED APPLICATIONS

This application is based upon and claims the benefit of priority from prior Japanese Patent Application No. 2008-040527, filed Feb. 21, 2008, the entire contents of which are incorporated herein by reference.

BACKGROUND OF THE INVENTION

1. Field of the Invention

The present invention relates to a manipulator operation system for a body cavity that performs an operation while observing a diseased part in a body cavity.

2. Description of the Related Art

In recent years, in, e.g., a surgical field, a manipulator operation system for a body cavity that performs an operation on behalf of an operator is known. The manipulator operation system has an endoscope or a treatment instrument, and operates, e.g., a grasping forceps at a distal end of the treatment instrument based on remote control by an operator to observe a diseased part in a body cavity. A bending portion coupled with the distal end of the treatment instrument or a bending portion of the endoscope usually has an articulated structure. Such a manipulator operation system moves each joint by using an actuator and thereby causes the distal end of the treatment instrument to easily approach (move closer to) a target region in a body cavity.

At this time, an imaging section, e.g., a CCD takes an image of the diseased part. This taken image is displayed in a display section, e.g., a monitor as an observation image. An operator operates an operating section, e.g., a joystick while visually observing the observation image. The treatment instrument is remotely operated with an operation (bending) amount with respect to an operation (input) amount for the operating portion by an operator so that the diseased part is given a treatment by, e.g., a grasping forceps in the treatment instrument.

For example, Jpn. Pat. Appln. KOKAI Publication No. H08-187246 discloses a manipulator apparatus for a body cavity operation in which operability of a handling skill is increased by moving a treatment instrument or a subject in an observation screen at a speed facilitating observation every time a manipulation is carried out.

Furthermore, for example, Jpn. Pat. Appln. KOKAI Publication No. H08-11071 discloses a manipulator control apparatus that allows a moving speed of a slave manipulator control point in a TV screen to constantly take a set value in accordance with an operation amount and an operation direction of an operator even though a focal distance of a camera, a distance from the camera to a slave manipulator control point, or a posture of the camera varies.

Moreover, Jpn. Pat. Appln. KOKAI Publication No. H 08-309680 discloses a manipulator control system that can always maintain a magnitude ratio of movement of an end point of a master arm and movement of a picture of an end point of a slave arm in a television monitor constant when a zoom ratio of an image input device is arbitrarily changed.

BRIEF SUMMARY OF THE INVENTION

It is, therefore, an object of the present invention to provide a manipulator operation system that can suppress a burden of an operation on an operator by adjusting a moving distance of a distal end of a treatment instrument in a display section with respect to an operation amount for an operating section by the operator.

According to the present invention, there is provided a manipulator operation system comprising: a treatment instrument distal end movement control section having an endoscope treatment instrument having a bending portion bendable in a desired direction and a distal end portion that is directly or indirectly coupled with the bending portion and has a treatment instrument that gives a diseased part a treatment, a bending driving section that drives the bending portion to bend, and a bending operating section that operates the bending driving section to bend the bending portion; imaging mechanism having an imaging section that includes an optical system having a field curvature, images the distal end portion and the bending portion by using the optical system, and provided separately from the endoscope treatment instrument; observing mechanism having a display section that displays as an observation image a taken image that is taken by the imaging section and has the field curvature; detecting mechanism having a detecting section that detects an arrangement position of the distal end portion that is imaged by the imaging section to be displayed in the display section; field curvature information acquiring mechanism having a field curvature information acquiring section that acquires field curvature information of the taken image; and adjusting mechanism having an adjustment section that adjusts a ratio of an operation amount of the bending operating section and a driving amount of the bending driving section based on the arrangement position detected by the detecting section and the field curvature information acquired by the field curvature information acquiring section.

Further, according to the present invention, there is provided a manipulator operation system comprising: a treatment instrument distal end movement control section having an endoscope treatment instrument having a bending portion bendable in a desired direction and a distal end portion that is directly or indirectly coupled with the bending portion and has a treatment instrument that gives a diseased part a treatment, a bending driving section that drives the bending portion to bend, a bending operating section that operates the bending driving section to bend the bending portion, and a detecting section that detects an arrangement position of the distal end portion; imaging mechanism having an imaging section that includes an optical system having a field curvature, images the distal end portion and the bending portion by using the optical system, and provided separately from the endoscope treatment instrument; calculating mechanism having a calculating section that calculates a relative distance from a distal end of the imaging section to the distal end portion from the arrangement position detected by the detecting section; observing mechanism having a display section that displays as an observation image a taken image that is taken by the imaging section and has the field curvature; field curvature information acquiring mechanism having a field curvature information acquiring section that acquires field curvature information of the taken image; and adjusting mechanism having an adjustment section that adjusts a ratio of an operation amount of the bending operating section and a driving amount of the bending driving section based on the relative distance calculated by the calculating section and the field curvature information acquired by the field curvature information acquiring section.

Advantages of the invention will be set forth in the description which follows, and in part will be obvious from the description, or may be learned by practice of the invention.

Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 8A is a view showing a state where the distal end portion is arranged at a central part in a monitor;

FIG. 8B is a view showing a state where the distal end portion is arranged at a central part periphery in the monitor;

DETAILED DESCRIPTION OF THE INVENTION

An embodiment according to the present invention will now be explained hereinafter with reference to the accompanying drawings.

A first embodiment will be explained in conjunction with FIGS. 1 to 10.

Figure 1:
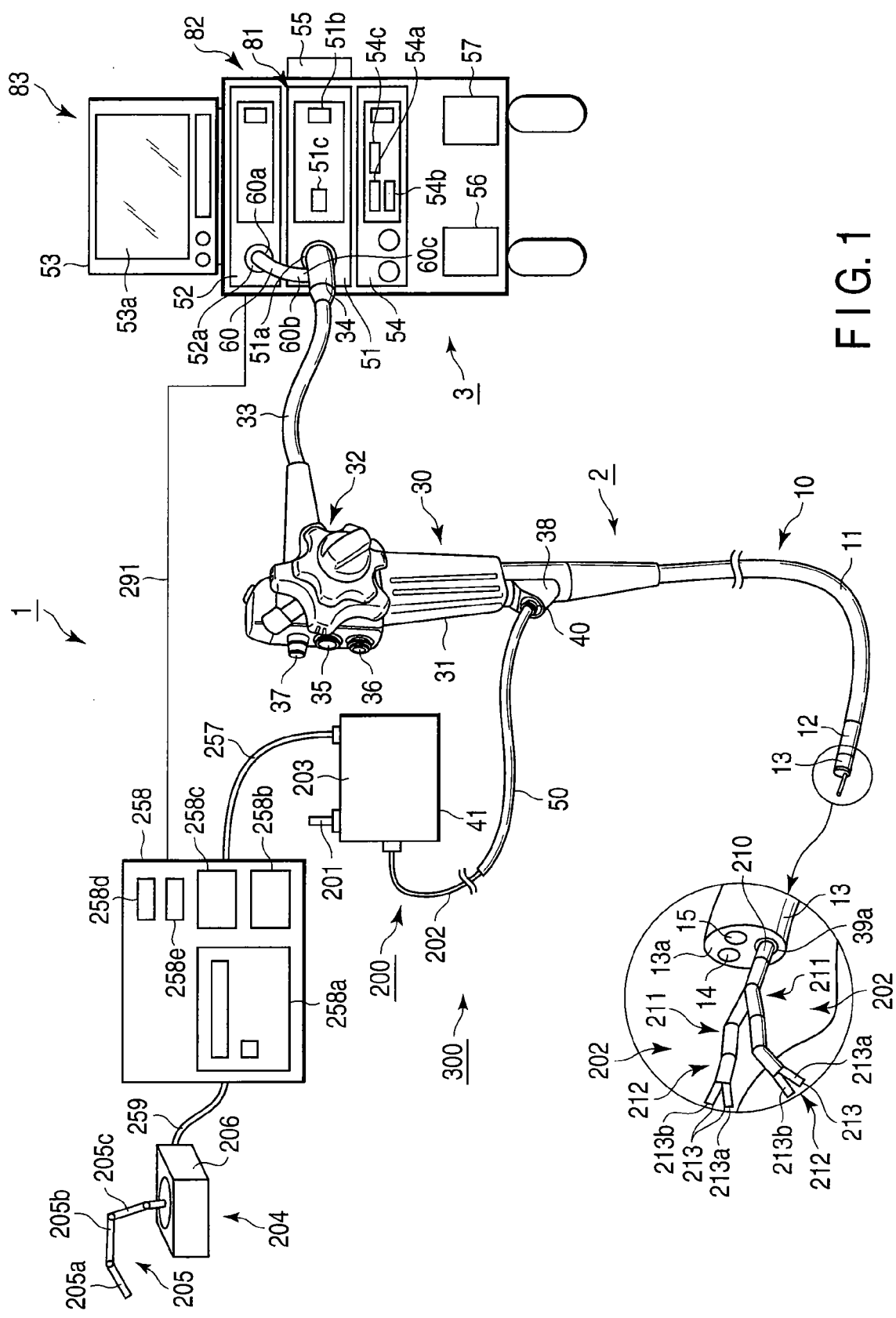
FIG. 1 is a view showing an outline structure of a manipulator operation system according to the present invention.

FIG. 1 is a view showing an outline structure of a manipulator operation system 1 according to this embodiment. The manipulator operation system 1 according to this embodiment has an endoscope 2 that can bend in a desired direction, a peripheral device (a device main body) 3 of the endoscope 2, a manipulator type electric endoscope treatment instrument 200 that is inserted into the endoscope 2 and gives a diseased part a treatment, and a treatment instrument distal end movement control device 300 that remotely operates the manipulator type electric endoscope treatment instrument 200.

In the endoscope 2 are provided an elongated inserting portion 10 that is inserted into, e.g., a body cavity of a patient and an operating section 30 that is coupled with a proximal end of the inserting portion 10 to operate the inserting portion 10.

To the operating section 30 are provided a grasping portion 31 grasped by an operator and a bending operation knob 32 that bends a later-explained bending portion 12 of the inserting portion 10.

A proximal end of the universal cord 33 is coupled with the grasping portion 31. A connector portion 34 connected with the peripheral device 3 is coupled with a distal end of this universal cord 33.

Furthermore, to the operating section 30 are provided a suction button 35, an air supply/water supply button 36, various endoscope imaging buttons 37, and a treatment instrument inserting portion 38. An insertion opening 40 of a later-explained treatment instrument insertion channel 39 is provided to the treatment instrument inserting portion 38. The endoscope treatment instrument 200 is inserted into this treatment instrument insertion channel 39.

A guide tube (an extension tube) 50 is detachably disposed to the insertion opening 40. The guide tube (the extension tube) 50 guides the endoscope treatment instrument 200 to the treatment instrument insertion channel 39 from the outside of the endoscope 2 through the insertion opening 40.

When the guide tube 50 is connected with the insertion opening 40 and the endoscope treatment instrument 200 is inserted into the guide tube 50, the guide tube 50 guides the endoscope treatment instrument 200 to the treatment instrument insertion channel 39. The endoscope treatment instrument 200 is inserted into the treatment instrument insertion channel 39 from the guide tube 50 through the insertion opening 40. Furthermore, the endoscope treatment instrument 200 is pushed to a later-explained distal end hard portion 13 side of the inserting portion 10 and then protruded (inserted) toward a body cavity from a distal end opening portion 39a of the treatment instrument insertion channel 39 depicted in FIG. 1.

The inserting portion 10 has a flexible tube portion (a corrugated tube portion) 11, the bending portion 12 that can freely bend in, e.g., upward, downward, left, and right directions, and the distal end hard portion 13 sequentially from the operating section 30 side. In more detail, the flexible tube portion 11 is formed of a resin and has a hollow elongated shape. The operating section 30 is coupled with a proximal end of the flexible tube portion 11. A distal end of the flexible tube portion 11 is coupled with a proximal end of the bending portion 12. A distal end of the bending portion 12 is coupled with a proximal end of the distal end hard portion 13.

The flexible tube portion 11 has elasticity and flexibility and bends with an external force. When the bending operation knob 32 is operated, non-illustrated operation wires are pulled, and the bending portion 12 bends in a desired upward, downward, left, or right direction. When the bending portion 12 bends, a position and a direction of the distal end hard portion 13 vary, and a desired observation target (e.g., a diseased part or an affected part) is captured in an observation view field (or an imaging view field).

The flexible tube portion 11 or the bending portion 12 is covered with a non-illustrated envelope tube.

On a distal end surface 13a of the distal end hard portion 13 are arranged the distal end opening portion 39a of the treatment instrument insertion channel 39, an observation window 14 that is included in imaging mechanism 80 and is a distal end of the imaging mechanism 80, an illumination window 15 included in irradiating mechanism 81, a non-illustrated air supply/water supply nozzle, and other components.

Figure 2:
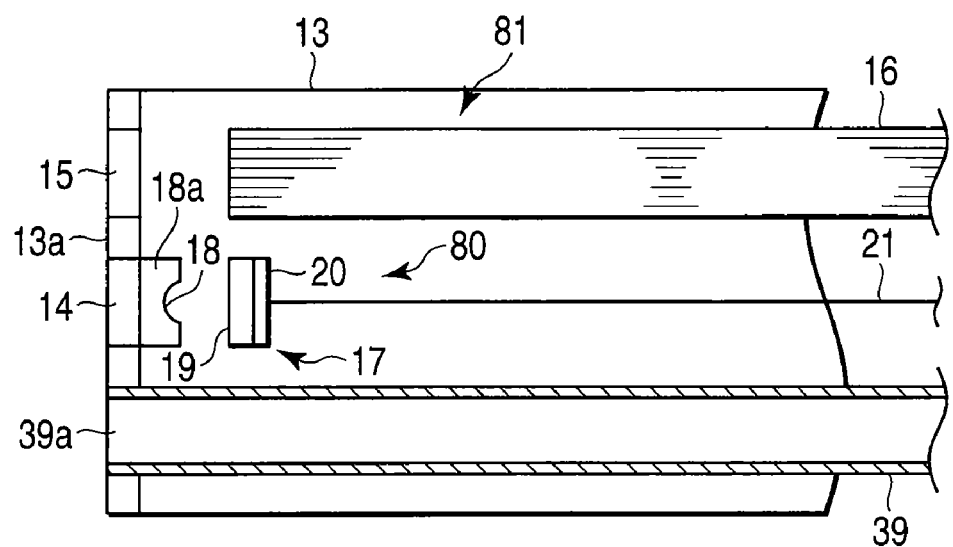
FIG. 2 is a schematic block diagram showing an internal structure of a distal end hard portion.
Figure 3A:
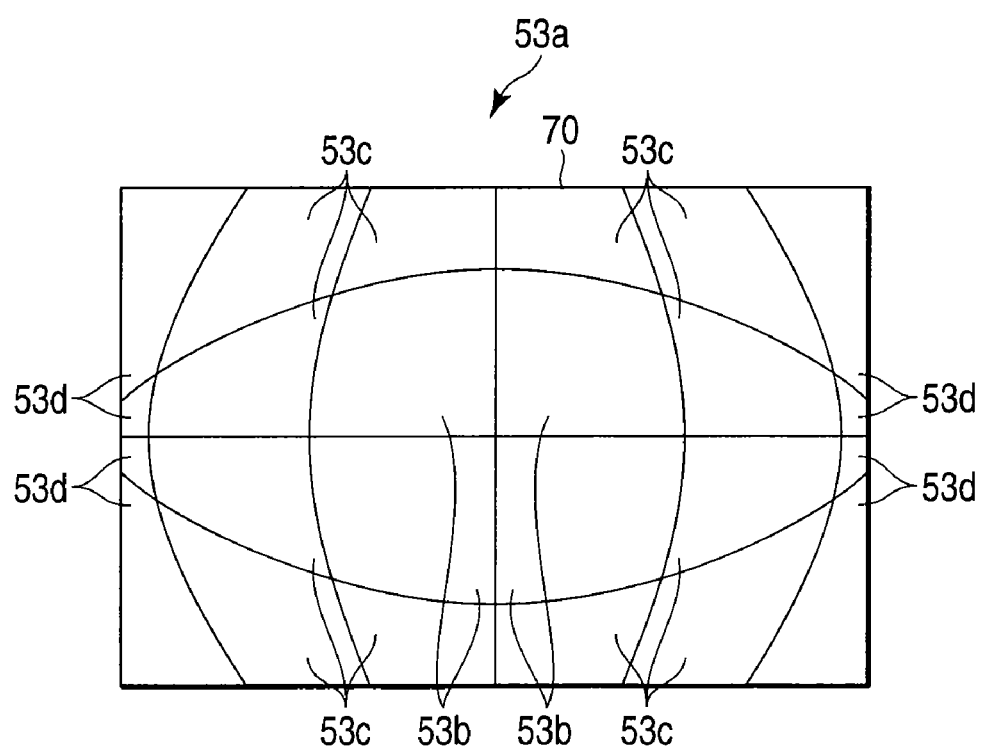
FIG. 3A is a view showing a monitor that displays a taken image having a field curvature.
Figure 4:
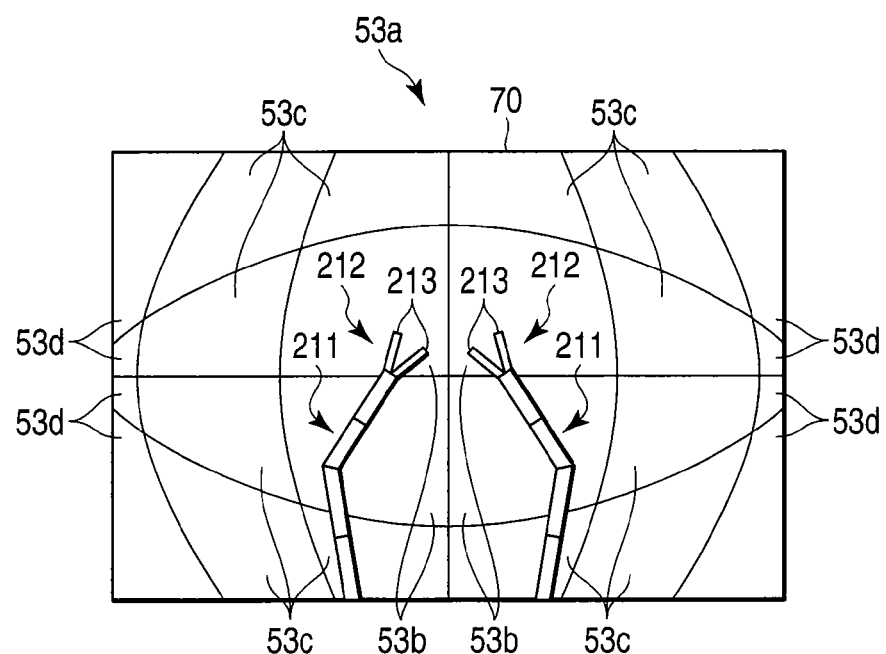
FIG. 4 is a view showing a monitor that displays a taken image having a field curvature when an endoscope treatment instrument protruding from a distal end opening portion is imaged.

As shown in FIG. 2, an imaging section 17 that is included in the imaging mechanism 80, takes an image 70 of, e.g., a diseased part depicted in FIG. 3A, and is provided separately from the endoscope treatment instrument 200 is fixed to the distal end hard portion 13 behind the observation window 14. The imaging section 17 includes an optical system 18, e.g., an object lens 18a having a desired field curvature, an imaging element 19 such as a CCD, a connection circuit board 20, and others. The object lens 18a, the imaging element 19, and the connection circuit board 20 are sequentially arranged from the observation window 14. The imaging section 17 uses, e.g., the optical system 18 to take image later-explained bending portion 211 and distal end portion 212 protruding (projecting) from the distal end opening portion 39a as depicted in FIG. 4.

Since the optical system 18 has a field curvature, the image 70 to be taken has a field curvature.

A cable 21, e.g., a signal line for the imaging element 19 is connected with the connection circuit board 20.

It is to be noted that the plurality of object lenses 18a may be arranged and at least some of these lenses can move in an axial direction. Therefore, the imaging element 19 can take an image of a diseased part in a state where a focal point of the image of the diseased part is formed on the imaging element 19 (the taken image 70 having the field curvature).

Moreover, a distal end of a non-illustrated image guide fiber may be fixed in place of the imaging element 19 so that the endoscope 2 can be provided as a fiber scope without being restricted to an electronic scope.

Additionally, as shown in FIG. 2, a distal end of a light guide fiber 16 included in the irradiating mechanism 81 is fixed to the distal end hard portion 13 behind the illumination window 15. The illumination window 15 is an irradiating section that irradiates a later-explained imaging range of the imaging section 17 with endoscope illumination light. The endoscope illumination light is generated by a later-explained light source device 51.

A distal end of the light guide fiber 16, the cable, a non-illustrated image guide fiber (case of the fiber scope), the treatment instrument insertion channel 39, a non-illustrated air supply tube, or a non-illustrated water supply tube is fixed to the distal end hard portion 13 as shown in FIG. 2. Furthermore, a proximal end of the light guide fiber 16, the cable, the non-illustrated image guide fiber (case of the fiber scope), the non-illustrated air supply tube, or the non-illustrate water supply tube is connected with the peripheral device 3 through the bending portion 12, the flexible tube portion 11, the operating section 30, and the universal cord 33. Moreover, a proximal end of the treatment instrument insertion channel 39 is connected with the insertion opening 40 through the bending portion 12, the flexible tube portion 11, and the operating portion 30 (the treatment instrument inserting portion 38).

In this embodiment, a situation where the two endoscope treatment instruments 200 are inserted into the one treatment instrument insertion channel 39 as shown in FIG. 1 is assumed. However, one or more endoscope treatment instruments 200 may be inserted into the one treatment instrument insertion channel 39. Additionally, the plurality of treatment instrument insertion channels 39 can be provided, and the endoscope treatment instruments 200 can be inserted into the respective treatment instrument insertion channels 39.

The peripheral device 3 has the light source device 51 that is included in the irradiating mechanism 81 and generates endoscope illumination light, an image processing device 52 that is included in field curvature information acquiring mechanism 82 and performs various kinds of image processing with respect to the image 70 taken by the imaging section 17, an image display device 53 that is included in observing mechanism 83 and has a monitor 53a as a display section that displays, e.g., an image, image data (an image taken by the imaging section 17 and subjected to image processing by the image processing device 52), a device state, or an operation instruction state, a control device 54 that carries out control over the entire manipulator operation system 1, arithmetic processing, and other components, an input device 55 including, e.g., a keyboard, a waste liquid tank device 56 with a suction pump, a water supply tank 57, and other components.

The light source device 51 has a connection opening 51a connected with the connector portion 34 and a display section 51b that displays an operating state of the light source device 51 on a front surface thereof.

The image processing device 52 has a connector receiver 52a connected with one end 60a of a connection cable 60 on a front surface thereof. A capped connecting portion 60c is provided at the other end 60b of the connection cable 60. A non-illustrated electrical connecting portion of the connector portion 34 is detachably connected with the capped connecting portion 60c.

The image processing device 52 is a field curvature information acquiring section that acquires field curvature information of the taken image 70 that is taken by the imaging section 17 and has a field curvature based on field curvature information of the optical system 18.

The field curvature information of the optical system 18 means field curvature information of the taken image 70, and it is information indicating how much the taken image 70 is distorted from a central part 53b of a monitor 53a (the taken image 70) toward a rim part 53d of the monitor 53a through a central part periphery 53c of the monitor 53a as shown in FIG. 3A.

Figure 3B:
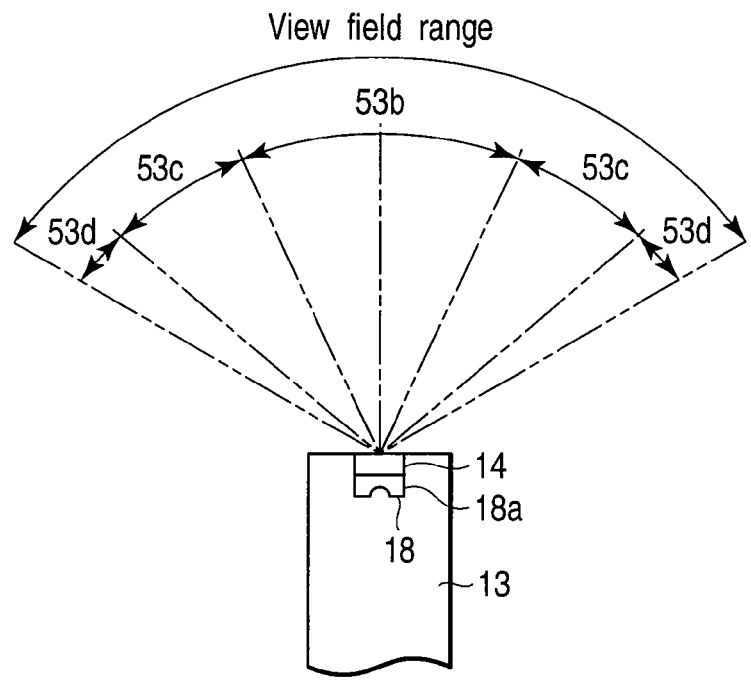
FIG. 3B is a view showing a view field range of an optical system.

As shown in FIG. 3A, the monitor 53a displays the taken image 70 that is taken by the imaging section 17 and has a field curvature as an observation image. Since the object lens 18a in the imaging section 17 has a field curvature, the taken image 70 has a field curvature. Therefore, distortion is increased from the central part 53b toward the rim part 53d through the central part periphery 53c. The range of the central part 53b, the central part periphery 53c, and the rim part 53d is affected by a view field range of the optical system 18 as shown in FIG. 3B.

Further, when the imaging section 17 images the later-explained bending portion 211 and distal end portion 212 protruding from the distal end opening portion 39a, the monitor 53a displays both the bending portion 211 and the distal end portion 212 as shown in FIG. 4.

In the control device 54 is provided a storage section 54a that stores each combination of optical characteristics (e.g., a magnification of the object lens 18a) and field curvature information of the optical system 18 associated with the optical characteristics. For example, when the endoscope 2 is connected with the peripheral device 3 (e.g., the image processing device 52) through the connector portion 34, optical characteristics of the optical system 18 are input to the control device 54. Connecting the endoscope 2 with the peripheral device 3 means connecting, e.g., the imaging section 17 included in the imaging mechanism 80 with, e.g., the image processing device 52 included in the field curvature information acquiring mechanism 82.

The control device 54 identifies the field curvature information of the optical system 18 associated with the input optical characteristics of the optical system 18 from combinations stored in the storage section 54*a*, and outputs this information to the image processing device 52. As a result, as explained above, the image processing device 52 acquires field curvature information of the taken image 70 that is taken by the imaging section 17 and has a field curvature based on the input field curvature information of the optical system 18.

It is to be noted that acquisition of the field curvature information is not restricted to the foregoing. For example, the field curvature information of the optical system 18 may be input to the input device 55. In more detail, when optical characteristics and other characteristics of the optical system 18, e.g., a magnification of the object lens 18*a* are input to the input device 55, the field curvature information is input. The input field curvature information is stored in, e.g., the storage section 54*a*. The control device 54 outputs the information to the image processing device 52 as in the above explanation. The image processing device 52 acquires field curvature information of the taken image 70 that is taken by the imaging section 17 and has a field curvature based on the field curvature information input by the input device 55. Further, a later-explained ratio of an operation amount and a bending amount is input to the input device 55 as desired.

The imaging mechanism 80 has the observation window 14 and the imaging section 17 (the optical system 18, the imaging element 19, and the connection circuit board 20), and is provided separately from the endoscope treatment instrument 200. The taken image 70 (an imaging signal) taken by the imaging section 17 is supplied to the image processing device 52 through the universal cord 33 and the connection cable 60.

The irradiating mechanism 81 has the illumination window 15, the light guide fiber 16, and the light source device 51 as an irradiating section.

The field curvature information acquiring mechanism 82 has the image processing device 52 as a field curvature information acquiring section. The image processing device 52 performs image processing with respect to the taken image 70 to be converted into a picture image (an observation image).

The observing mechanism 83 has the image display device 53 including the monitor 53*a*. The image display device 53 displays the taken image 70 that is taken by the imaging section 70 and has a field curvature in the monitor 53*a* as an observation image.

The endoscope treatment instrument 200 according to this embodiment will now be explained.

Figure 5:
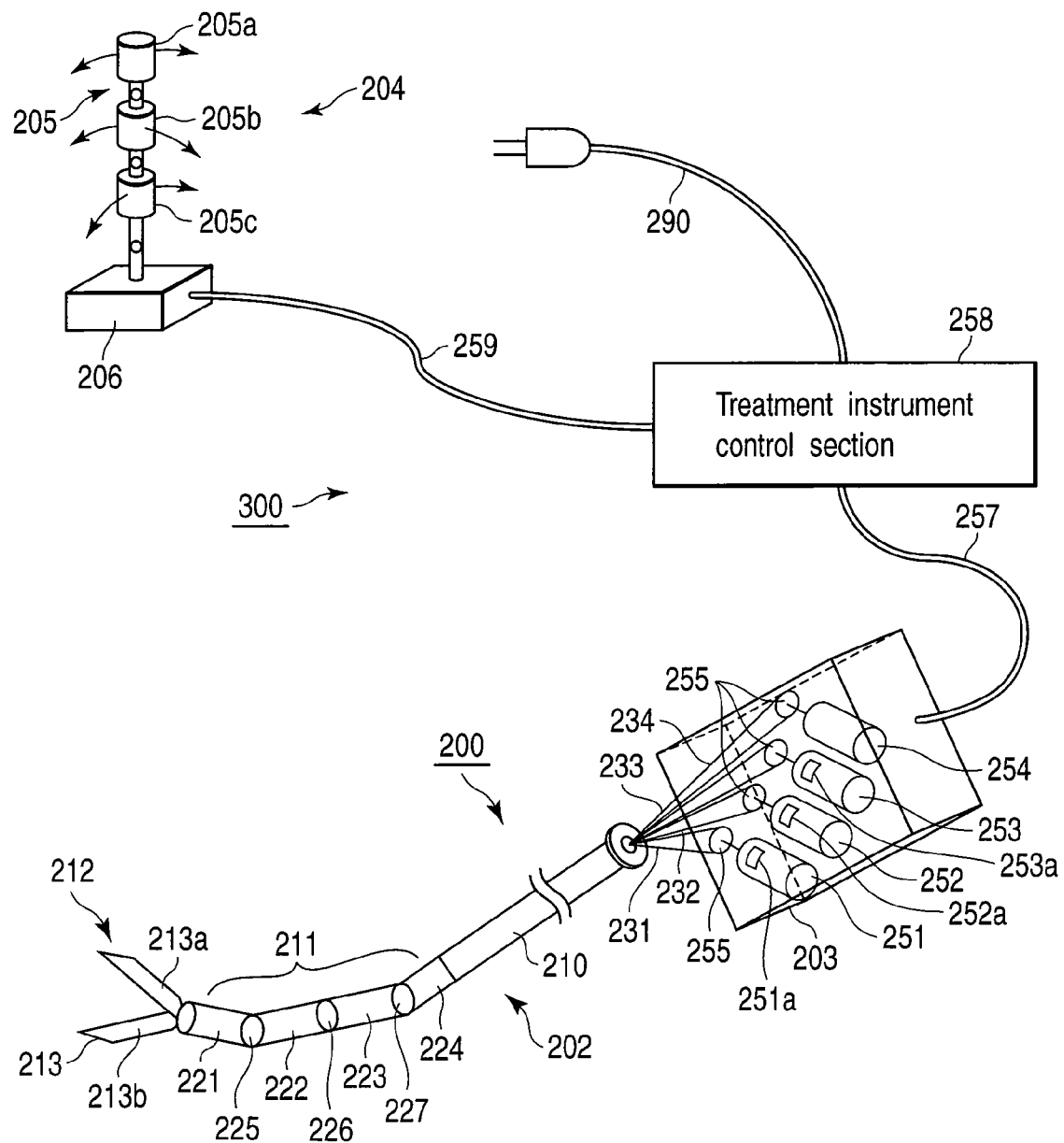
FIG. 5 is a perspective view schematically showing a treatment instrument distal end movement control device including the endoscope treatment instrument.
Figure 6:
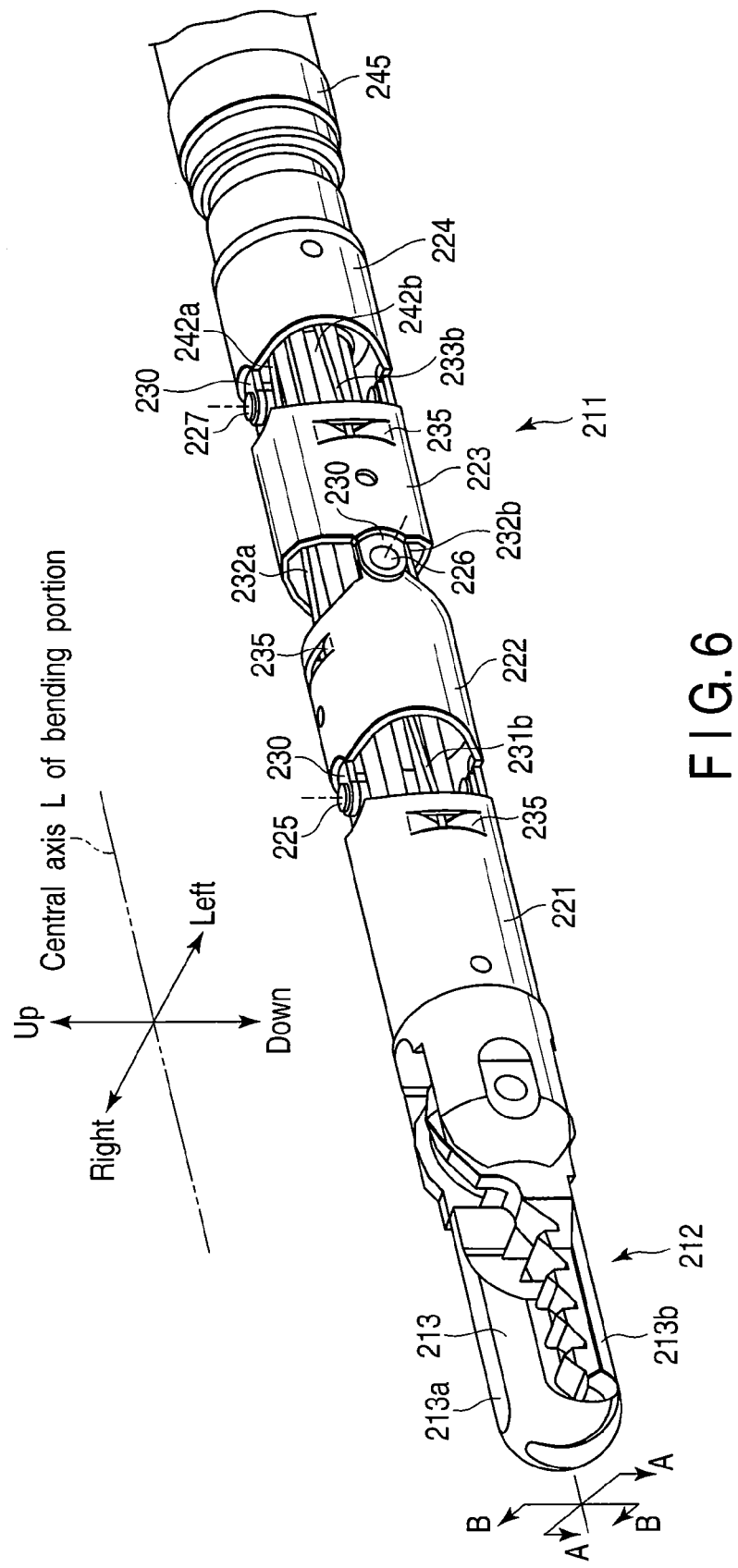
FIG. 6 is a perspective view showing a distal end portion and a bending portion in an inserting portion of the endoscope treatment instrument.

The endoscope treatment instrument 200 that gives a diseased part a treatment has an articulated bending mechanism as shown in FIGS. 1, 5, and 6. The endoscope treatment instrument 200 has an inserting portion 202 inserted into a body cavity and a driving unit 203 coupled with the inserting portion 202. The driving unit 203 is a bending driving section that moves forward or backward the inserting portion 202 in an inserting direction of the endoscope 2 and drives the bending portion 211 in the inserting portion 202 to bend. A treatment instrument operating section 201 that operates a later-explained grasping forceps 213 is provided to the driving unit 203.

As shown in FIG. 1, the inserting portion 202 is protruded (inserted) into a body cavity from the distal end opening portion 39*a* through the guide tube 50, the insertion opening 40, and the treatment instrument insertion channel 39. As shown in FIGS. 5 and 6, the inserting portion 202 has a flexible tube portion (a soft portion) 210 placed on an operator's hand (proximal end) side, a bending portion 211 coupled with a distal end of the flexible tube portion 210, and a distal end portion 212 directly or indirectly coupled with a distal end of the bending portion 211.

The flexible tube portion 210 has elasticity and flexibility and is bent by an external force.

The bending portion 211 has an articulated bending mechanism and bends in a desired one of upward, downward, left, and right directions.

The distal end portion 212 has the grasping forceps 213 as a treatment instrument main body portion (a treatment instrument) that gives, e.g., a diseased part a treatment. The grasping forceps 213 has grasping members 213*a* and 213*b* shown in FIGS. 5 and 6 that are vertically opened and closed by later-explained operation wires 234. The operation wires 234 are inserted into the inserting portion 202. A member provided to the distal end portion 212 is not restricted to the grasping forceps 213, and a treatment instrument, e.g., a radio-frequency knife or a radio-frequency coagulator may be provided, for example.

The bending portion 211 will now be explained in detail with reference to FIGS. 5 and 6. The bending portion 211 has a node ring 221, a node ring 222, a node ring 223, and a node ring 224. Coupling the node ring 221, the node ring 222, the node ring 223, and the node ring 224 forms the bending portion 211. It is to be noted that the number of the node rings to be coupled does not have to be restricted to four, and providing at least two node rings can suffice. Each of the node ring 221, the node ring 222, the node ring 223, and the node ring 224 is formed of a ring-shaped member, and these node rings are coaxially aligned and arranged in a longitudinal direction of the inserting portion 202. The node ring 221, the node ring 222, the node ring 223, and the node ring 224 adjacent each other are coupled to allow their swiveling portions to swivel (moving rotationally). As a result, the articulated bending mechanism is constituted.

Figure 7A:
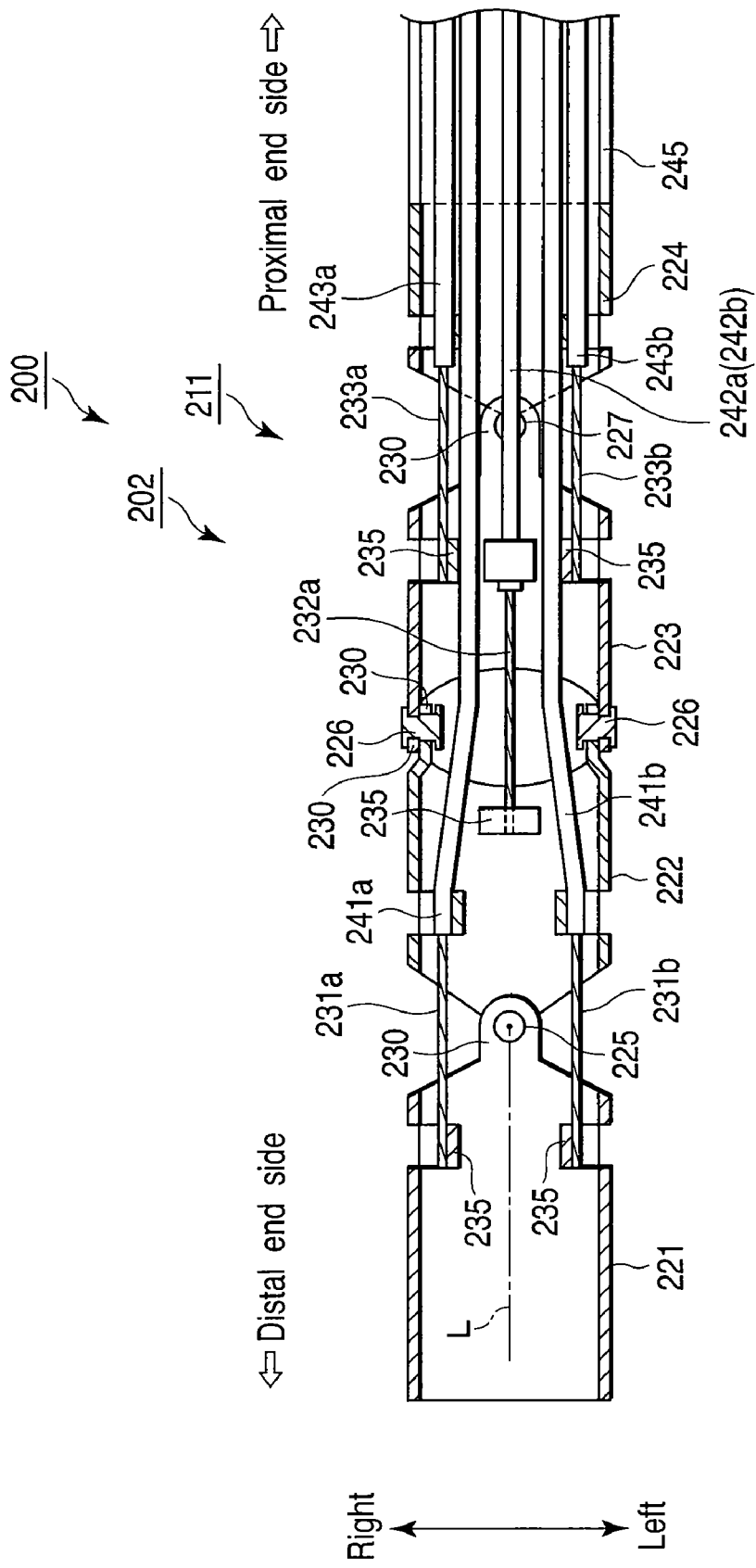
FIG. 7A is a cross-sectional view showing from above a cross section obtained by vertically cutting the bending portion in a longitudinal direction of the inserting portion at a horizontal plane indicated by an arrow line A-A in FIG. 6.
Figure 7B:
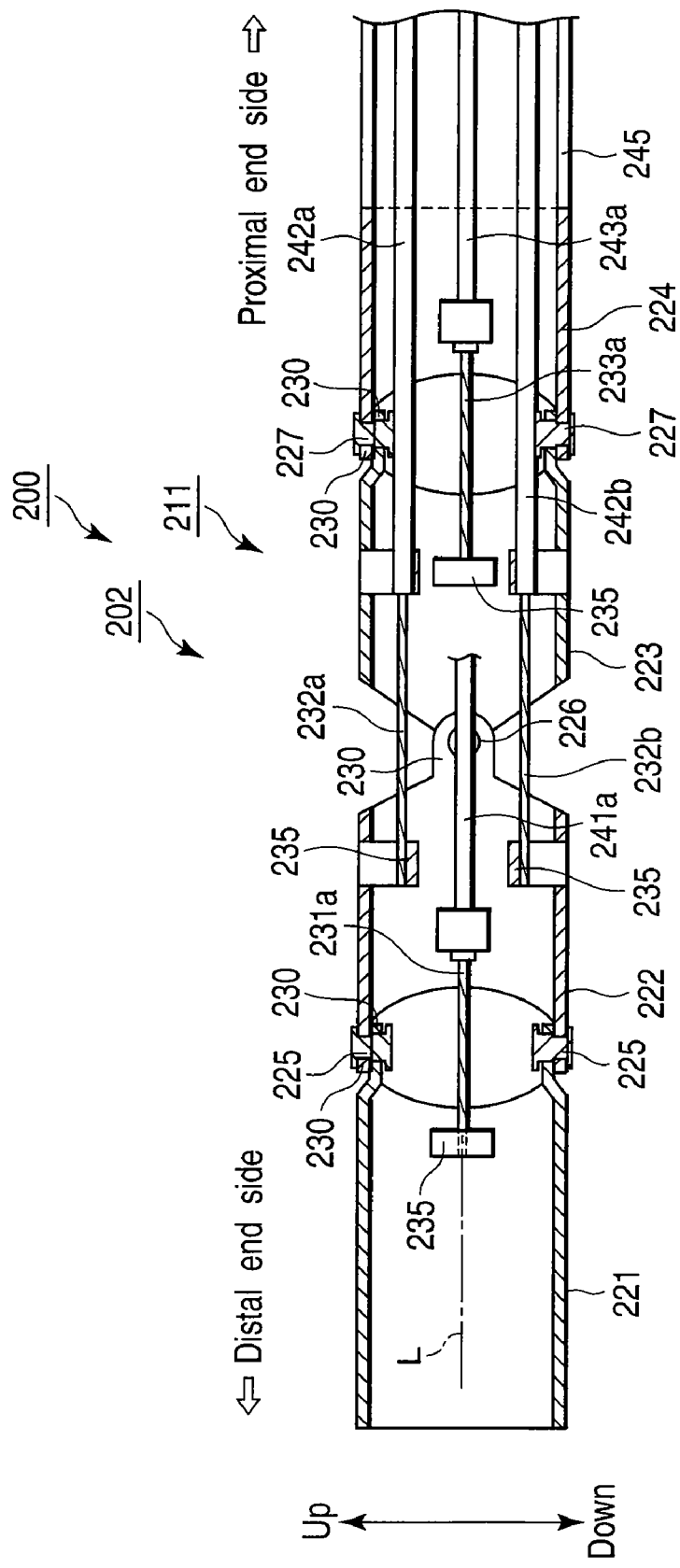
FIG. 7B is a cross-sectional view showing from a left-hand side a cross section obtained by vertically cutting the bending portion in the longitudinal direction of the inserting portion at a vertical plane indicated by an arrow line B-B in FIG. 6.

FIG. 7A is a cross-sectional view showing from above a cross section obtained by vertically cutting the bending portion 211 in the longitudinal direction of the inserting portion 202 at a horizontal plane indicated by an arrow line A-A in FIG. 6. FIG. 7B is a cross-sectional view showing from a left-hand side a cross section obtained by vertically cutting the bending portion 211 in the longitudinal direction of the inserting portion 202 at a vertical plane indicated by an arrow line B-B in FIG. 6. Upward, downward, left, and right directions of the bending portion 211 conform to an index depicted in FIG. 6.

The node ring 221 and the node ring 222 are connected to allow their swiveling motion around a first swiveling shaft portion 225 and coupled by the first swiveling shaft portion 225 to allow their swiveling motion. The first swiveling shaft portion 225 has an axial direction orthogonal to the longitudinal direction of the inserting portion 202 and is arranged in a direction parallel to a vertical direction depicted in FIG. 6. Therefore, the node ring 221 and the node ring 222 can relatively swivel in a lateral direction as seen from an operator's hand (proximal end) side in FIG. 6.

The node ring 222 and the node ring 223 are connected to allow their swiveling motion around a second swiveling shaft portion 226 and coupled by the second swiveling shaft portion 226 to allow their swiveling motion. The second swiveling shaft portion 226 has an axial direction orthogonal to the longitudinal direction of the inserting portion 202 and is arranged in a direction parallel to the lateral direction depicted in FIG. 6. Therefore, the node ring 222 and the node ring 223 can relatively swivel in the vertical direction as seen from the operator's hand (proximal end) side in FIG. 6.

The node ring 223 and the node ring 224 are connected to allow their swiveling motion around a third swiveling shaft portion 227 and coupled by the third swiveling shaft portion 227 to allow their swiveling portion. The third swiveling shaft portion 227 has an axial direction orthogonal to the longitudinal direction of the inserting portion 202 and is arranged in a direction parallel to the vertical direction depicted in FIG. 6. Therefore, the node ring 223 and the node ring 224 can relatively swivel in the lateral direction as seen from the operator's hand (proximal end) side in FIG. 6.

That is, the first swiveling shaft portion 225 forms a joint that relatively swivels the node ring 221 and the node ring 222 in the lateral direction. Further, the second swiveling shaft portion 226 forms a joint that relatively swivels the node ring 222 and the node ring 223 in the vertical direction. Furthermore, the third swiveling shaft portion 227 forms a joint that relatively swivels the node ring 223 and the node ring 224 in the lateral direction.

In this embodiment, the axial directions of the first swiveling shaft portion 225, the second swiveling shaft portion 226, and the third swiveling shaft portion 227 are alternately shifted at 90°. That is, the node rings 221 and 222 and the node rings 223 and 224 swivel in the lateral direction. Moreover, the node rings 222 and 223 swivel in the vertical direction. Additionally, the axial directions of the swiveling shaft portions 225, 226, and 227 are orthogonal to a central axis (a long axis) L of the bending portion 211 (see FIGS. 6, 7A, and 7B). This central axis L coincides with a long axis of the inserting portion 202.

As shown in FIGS. 7A and 7B, a tongue-piece-like coupling portion 230 protruding from each edge is provided to each of the node rings 221, 222, 223, and 224. When the coupling portions 230 overlap each other, the swiveling shaft portions 225, 226, and 227 pierce overlapping parts. That is, each of the swiveling shaft portions 225, 226, and 227 is a rivet-like shaft member.

The thus configured articulated bending mechanism is covered with a soft envelope (not shown). As a result, the bending portion 211 is constituted.

As shown in FIGS. 7A and 7B, in the inserting portion 202 are inserted a first pair of non-flexible operation wires 231 (231a, 231b) connected with the node ring 221, a second pair of non-flexible operation wires 232 (232a, 232b) connected with the node ring 222, and a third pair of non-flexible operation wires 233 (233a, 233b) connected with the node ring 223.

As shown in FIG. 7A, the operation wires 231a and 231b are laterally symmetrically arranged with the central axis L at the center in the bending portion 211. Distal ends of the operation wires 231a and 231b are extended to a region in the node ring 221 to be connected with the node ring 221.

A direction of a central axis of the node ring 221 substantially coincides with a direction of the central axis L. In a plane running through both the direction of the central axis of the node ring 221 and the axial direction of the first swiveling shaft portion 225, a right half of the node ring 221 is determined as a right region and a left half of the node ring 221 is determined as a left region.

The distal end of the operation wire 231a is connected with the right region of the node ring 221. Further, the distal end of the operation wire 231b is connected with the left region of the node ring 221. When the operation wire 231a is pulled toward the proximal end (operation's hand) side depicted in FIG. 7A, the node ring 221 swivels toward the right-hand side with the first swiveling shaft portion 225 at the center. Furthermore, when the operation wire 231b is pulled toward the proximal end side, the node ring 221 swivels toward the left-hand side with the first swiveling shaft portion 225 at the center. In this manner, the operation wires 231 swivel the node ring 221.

As shown in FIG. 7B, the operation wires 232a and 232b are vertically symmetrically arranged with the central axis L at the center in the bending portion 211. Distal ends of the operation wires 232a and 232b are extended to a region in the node ring 222 to be connected with the node ring 222.

A direction of a central axis of the node ring 222 substantially coincides with the direction of the central axis L. In a plane running through both the direction of the central axis of the node ring 222 and the axial direction of the second swiveling shaft portion 226, an upper half of the node ring 222 is determined as an upper region and a lower half of the node ring 222 is determined as a lower region.

The distal end of the operation wire 232a is connected with the upper region of the node ring 222. Moreover, the distal end of the operation wire 232b is connected with the lower region of the node ring 222. When the operation wire 232a is pulled toward the proximal end (operator's hand) side depicted in FIG. 7B, the node ring 222 swivels upward with the second swiveling shaft portion 226 at the center. Additionally, when the operation wire 232b is pulled toward the proximal end side depicted in FIG. 7B, the node ring 222 swivels downward with the second swiveling shaft portion 226 at the center. In this manner, the operation wires 232 swivel the node ring 222.

As shown in FIG. 7A, the operation wires 233a and 233b are laterally symmetrically arranged with the central axis L at the center in the bending portion 211. Distal ends of the operation wires 233a and 233b are extended to a region in the node ring 223 to be connected with the node ring 223.

A direction of a central axis of the node ring 223 substantially coincides with the direction of the central axis L. In a plane running through both the direction of the central axis of the node ring 223 and the axial direction of the third swivel shaft portion 227, a right half of the node ring 223 is determined as a right region and a left half of the node ring 223 is determined as a left region.

The distal end of the operation wire 233a is connected with the right region of the node ring 223. Further, the distal end of the operation wire 233b is connected with the left region of the node ring 223. When the operation wire 233a is pulled toward the proximal end (operator's hand) side depicted in FIG. 7A, the node ring 223 swivels toward the right-hand side with the third swivel shaft portion 227 at the center. Furthermore, when the operation wire 233b is pulled toward the proximal end side depicted in FIG. 7A, the node ring 223 swivels toward the left-hand side with the third swivel shaft portion 227 at the center. In this manner, the operation wires 233 swivel the node ring 223.

As explained above, each of the corresponding pairs of the operation wires 231, 232, and 233 is connected with each of the node rings 221, 222, and 223. In the bending portion 211, when the pair of operation wires 231, 232, or 233 are appropriately selected and pushed or pulled, the node ring 221, 222, or 223 independently swivels.

As a result, the articulated mechanism is formed, and the bending portion 211 can be bent in the four direction, i.e., the upward, downward, left, and right directions.

It is to be noted that various kinds of methods can be adopted as means for connecting the distal ends of the operation wires 231, 232, and 233 with the node rings 221, 222, and 223, and fixation based on brazing can be carried out, for example.

As shown in FIG. 7A, at the proximal end of the node ring 221, a cut-and-raised piece 235 protruding toward the inside of the node ring 221 is formed in each of the right region and the left region of the node ring 221. The distal end of the operation wire 231a is inserted into the cut-and-raised piece 235 in the right region and brazed to this cut-and-raised piece 235. Further, the distal end of the operation wire 231b is inserted into the cut-and-raised piece 235 in the left region and brazed to this cut-and-raised piece 235.

Furthermore, as shown in FIG. 7B, at the proximal end of the node ring 222, the cut-and-raised piece 235 protruding toward the inside of the node ring 222 is formed in each of the upper region and the lower region of the node ring 222. The distal end of the operation wire 232a is inserted into the cut-and-raised piece 235 in the upper region and brazed to this cut-and-raised piece 235. Moreover, the distal end of the operation wire 232b is inserted into the cut-and-raised piece 235 in the lower region and brazed to this cut-and-raised piece 235.

Additionally, as shown in FIG. 7A, in a periphery of the proximal end of the node ring 223, the cut-and-raised piece 235 protruding toward the inside of the node ring 223 is formed in each of the right region and the left region of the node ring 223. The distal end of the operation wire 233a is inserted into the cut-and-raised piece 235 in the right region and brazed to this cut-and-raised piece 235. Further, the distal end of the operation wire 233b is inserted into the cut-and-raised piece 235 in the left region and brazed to this cut-and-raised piece 235.

Furthermore, the operation wires 231 are inserted into guide sheaths 241, the operation wires 232 are inserted into guide sheaths 242, the operation wires 233 are inserted into guide sheaths 243, and they are individually led to the driving unit 203. Each of the guide sheaths 241, 242, and 243 has flexibility and is formed of a sheath-like elastic member having elasticity, e.g., a close coil or a resin tube. An inner hole of each of the guide sheaths 241, 242, and 243 is a guide member that guides a moving direction of each of the operation wires 231, 232, and 233.

A distal end of each guide sheath is connected with the node ring that is arranged on a proximal end side rather than the node guide connected with the operation wire guided by this guide sheath. For example, distal ends of the guide sheaths 241a and 241b are connected with the node ring 222. Moreover, distal ends of the guide sheaths 242a and 242b are connected with the node ring 223.

In more detail, the distal end of each guide sheath is fixed to a wire guide provided to each node ring. It is to be noted that each of the guide sheaths 241, 242, and 243 may be indirectly fixed to the wire guide by using a non-illustrated connection instrument, e.g., a connection mouth ring.

A proximal end of each of the guide sheaths 241, 242, and 243 may be connected with the proximal end of the bending portion 211 (the distal end of the flexible tube portion 210).

The node ring connected with the distal end of the guide sheath is not the guide sheath connected with the operation wire guided by this guide sheath but the node ring arranged closer to the proximal end side than the node ring connected with this operation wire. Therefore, the distal end of the operation wire protruding from the distal end of the guide sheath is connected with the node ring arranged closer to the distal end than the node ring connected with the distal end of the guide sheath. That is, the operation wire is inserted into and guided through the guide sheath until it reaches the node ring arranged closer to the proximal end side than the node ring connected with this operation wire. Therefore, the operation wire led by the guide sheath does not directly come into contact with the contents, e.g., any other operation wire or the guide sheath, thereby avoiding interference.

It is to be noted that, as shown in FIG. 6, the node ring 224 is the node ring arranged at the most proximal end of the bending portion 211. That is, the node ring 224 can be regarded as the proximal end of the bending portion 211. A connection member 245, e.g., a connection mouth ring is provided at the distal end of the flexible tube portion 210. The node ring 224 is coupled with the connection member 245. Furthermore, the node ring 224 may be coupled with the connection member 245 to allow its swiveling motion. In this case, the connection member 245 is regarded as the proximal end of the bending portion 211.

As shown in FIG. 5, a bending portion operating mechanism and a treatment section operating mechanism are provided to the driving unit 203.

The bending portion operating mechanism includes driving motors 251, 252, and 253 that push or pull the operation wires 231, 232, and 233, respectively.

Moreover, the treatment section operating mechanism includes a driving motor 254 that pushes or pulls the operation wires 234.

The operation wires 231, 232, and 233 are associated with the node rings 221, 222, and 223 as swiveling operation targets, and operate for swiveling. The operation wires 234 operate the grasping forceps 213.

A pulley 255 is disposed to a driving shaft of each of the driving motors 251, 252, 253, and 254. Each driving shaft may be also coupled with each pulley 255 through a non-illustrated reducer. The operation wires 231, 232, 233, and 234 are wound around the respective pulleys 255. Additionally, when the driving motors 251, 252, 253, and 254 individually drive and the pulleys 255 swivel, the operation wires 231, 232, 233, and 234 wound around the pulleys 255 are pushed or pulled.

Although a transmission mechanism utilizing the pulleys 255 is adopted as the bending portion operating mechanism and the treatment section operating mechanism, it may be a gear mechanism or the like utilizing a pinion gear or a rack, for example. Further, in the bending portion operating mechanism and the treatment section operating mechanism, driving actuators of any other type may be used in place of the driving motors 251, 252, 253, and 254.

As shown in FIGS. 1 and 5, the driving unit 203 is connected with a treatment instrument control section 258 through a cable 257. A bending operating section 204 as an operation input device is connected with the treatment instrument control section 258 through a cable 259. Furthermore, to the treatment instrument control section 258 are provided a power supply cord 290 and a connection cable 291 connected with the peripheral device (e.g., the light source device 51 and the image processing device 52) as shown in FIG. 5 and FIG. 1.

The bending operating section 204 has, e.g., a joystick (an operation input device) 205 that is operated by an operator to instruct a position and a posture of the endoscope treatment instrument 200, for example. This joystick 205 has three joystick switches 205a, 205b, and 205c coupled on three tiers. The joystick switches 205a, 205b, and 205c are disposed to an operation box 206.

It is to be noted that FIG. 5 shows the driving unit 203, the treatment instrument control section 258, and the bending operating section 204 with respect to one endoscope treatment instrument 200. Moreover, in this embodiment, as shown in FIG. 1, the two endoscope treatment instruments 200 are inserted into the one treatment instrument insertion channel 39. Therefore, although the driving unit 203, the treatment instrument control section 258, and the bending operating section 204 are arranged with respect to each of the two endoscope treatment instruments 200, FIG. 1 shows the single driving unit 203, the single treatment instrument control section 258, and the single bending operating section 204 to simplify the drawing.

As shown in FIG. 1, to the treatment instrument control section 258 are provided a function control input section 258a that inputs, e.g., conditions for control over instructions output from the joystick 205 or functions of the joystick 205, a motor driver (a treatment instrument driving control section) 258b that controls to drive the driving motors 251, 252, and 253, and a motor unit communicating section 258c that is connected with the driving unit 203 through the cable 257 to perform communication with the driving unit 203.

When the joystick switch 205a, 205b, or 205c is selectively operated, the treatment instrument control section 258 transmits a control signal required to drive the driving motor 251, 252, or 253 in accordance with an operation of the joystick 205 by an operator to the motor driver 258b, thereby rotating the driving motor 251, 252, or 253. That is, the driving motor 251, 252, or 253 is individually driven in accordance with an operation of the joystick 205. As a result, the operation wires 231, 232, or 233 are pushed or pulled by the swiveling pulley 255, the node ring 221, 222, or 223 is individually independently swiveled in the upward, downward, left, or right direction, and each joint is curved. That is, the bending portion 211 is bent.

In this manner, the bending operating section 204 is an operation input device that operates the driving unit 203 to bend the bending portion 211.

The treatment instrument distal end movement control device 300 includes the endoscope treatment instrument 200 having the bending portion 211 and the distal end portion 212, the driving unit (the bending driving section) 203, the treatment instrument operating section 201, and the bending operating section (the operation input device) 204 as shown in FIGS. 1 and 5. Additionally, the treatment instrument distal end movement control device 300 may include the treatment instrument control section 258. Further, the treatment instrument distal end movement control device 300 can move the distal end portion 212 to a desired position based on movement conforming to an operation of the joystick 205. That is, the treatment instrument distal end movement control device 300 constitutes the manipulator (master-slave) type electric endoscope treatment instrument 200. It is to be noted that, when the joystick 205 is operated by, e.g., an operator after control to move the endoscope treatment instrument 200 is set, a priority is given to an operation command of the joystick 205.

It is to be noted that encoders 251a, 252a, and 253a that measure numbers of revolutions of the respective motors are disposed to the driving motors 251, 252, and 253 as shown in FIG. 5. Each of the encoders 251a, 252a, and 253a generates a signal associated with the number of revolutions of each driving motor and transmits the generated signal to the motor driver 258b to perform feedback control over each of the driving motors 251, 252, and 253.

To the treatment instrument control section 258 is provided a detecting section 258d that detects a signal generated by the encoder 251a, 252a, or 253a through the motor driver 258b and detects an arrangement position of the distal end portion 212 (the grasping forceps 213) based on the detected signal.

The treatment instrument control section 258 serves as detecting mechanism having the detecting section 258d.

In more detail, the detecting section 258d detects (calculates) a swiveling angle in each of the node rings 221, 222, and 233, i.e., a bending angle of each joint. The detecting section 258d detects an arrangement position of the distal end portion 212 based on the detected bending angle. It is to be noted that, for example, when the bending portion 211 and the grasping forceps 213 protrude from the distal end opening portion 39a as shown in FIG. 1 and the bending portion 211 and the grasping forceps 213 are displayed in the monitor 53a (the taken image 70), the detecting section 258d detects an arrangement position of the distal end portion 212 in the monitor 53a.

Further, to the treatment instrument control section 258 is provided an adjustment section 258e that adjusts a ratio of an operation amount of the joystick 205 by, e.g., an operator and a bending amount of the bending portion 211 (which will be referred to as a ratio of an operation amount and a bending amount hereinafter) based on an arrangement position of the distal end portion 212 detected by the detecting section 258d and field curvature information acquired by the image processing device 52 as the field curvature information acquiring section through the connection cable 291 and thereby controls the driving unit 203. As a brief explanation, the adjustment section 258e adjusts a ratio of an operation amount and a bending amount based on an arrangement position of the distal end portion 212 and field curvature information acquired by the image processing device 52 and controls the driving unit 203. The treatment instrument control section 258 serves as adjusting mechanism having the adjustment section 258e.

The bending amount of the bending portion 211 is a driving amount of the driving unit 203 (the driving motors 251, 252, and 253), and it is a moving distance (a moving speed, a moving (operation) amount) of the distal end portion 212 (the grasping forceps 213) and the bending portion 211 in the monitor 53a. A moving distance of the distal end portion 212 and the bending portion 211 will be referred to as a moving distance hereinafter.

When the detecting section 258d detects that the distal end portion 212 is arranged at the central part 53b as shown in FIG. 8A and the image processing device 52 acquires field curvature information, the adjustment section 258e adjusts a ratio of an operation amount and a bending amount to, e.g., 1:1, and controls the driving unit 203 (the driving motors 251, 252, and 253).

Furthermore, when the detecting section 258d detects that the distal end portion 212 is arranged at the central part periphery 53c as shown in FIG. 8B and the image processing device 52 acquires field curvature information, the adjustment section 258e adjusts a ratio of an operation amount and a bending amount to, e.g., 1:1/3, and controls the driving unit 203.

Figure 8C:
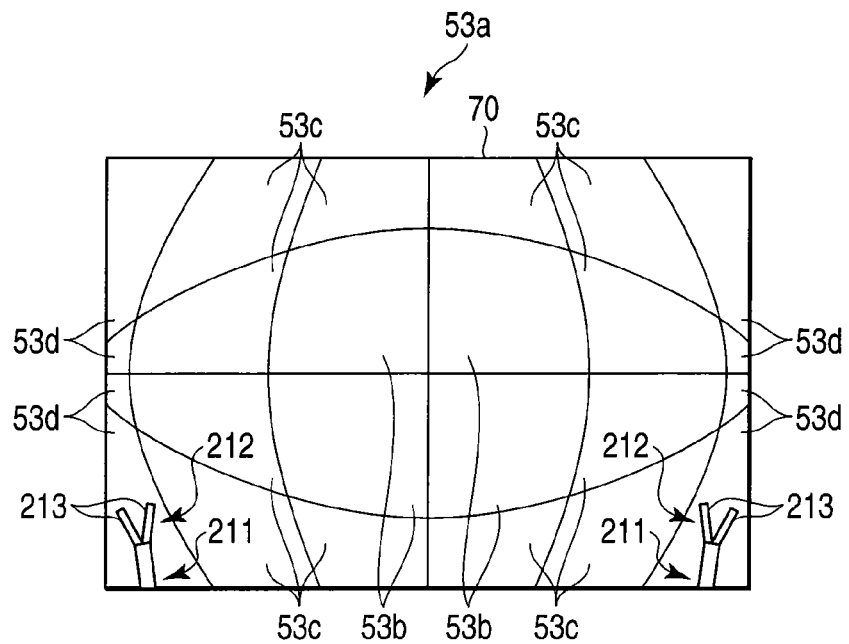
FIG. 8C is a view showing a state where the distal end portion is arranged at a rim part in the monitor.

Moreover, when the detecting section 258d detects that the distal end portion 212 is arranged at the rim part 53d as shown in FIG. 8C and the image processing device 52 acquires field curvature information, the adjustment section 258e adjusts a ratio of an operation amount and a bending amount to, e.g., 1:1/5, and controls the driving unit 203.

In general, even if an operation amount of the joystick 205 required to operate the bending portion 211 is unchanged, a moving distance (a moving speed, a moving (operation) amount) on the monitor 53a is differently displayed depending on the central part 53b, the central part periphery 53c, and the rim part 53d based on a field curvature of the imaging section 17.

Figure 9A:
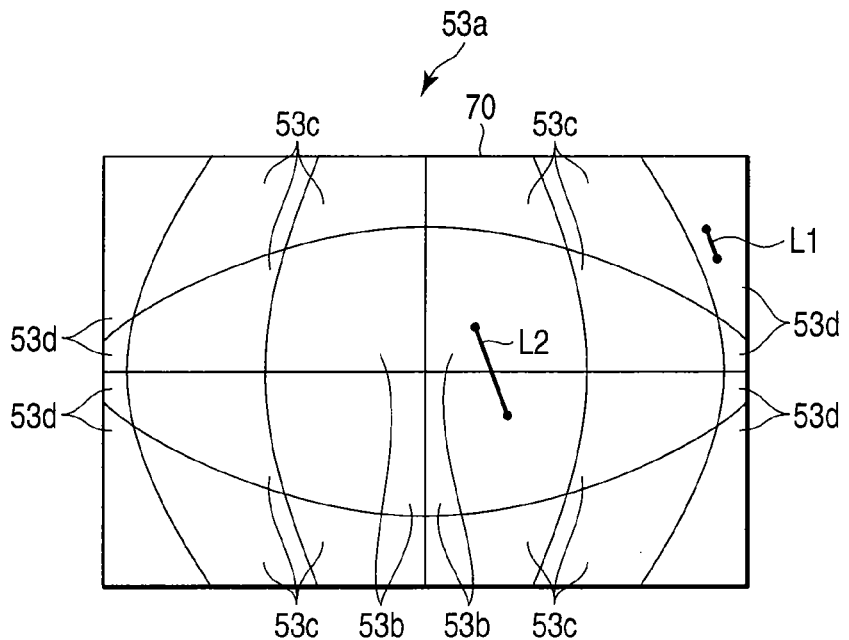
FIG. 9A is a view showing the monitor in which a moving distance at the rim part is displayed to be longer than a moving distance at the central part.

In detail, when the operation amount is the same, a moving distance at the rim part 53d is displayed to be shorter (a moving speed is higher and a moving amount is smaller) than a moving distance at the central part 53b. That is, even if the operation amount is the same, a moving distance with respect to the operation amount is differently displayed on the monitor 53a (at the central part 53b, the central part periphery 53c, and the rim part 53d). For example, as shown in FIG. 9A, a moving distance L1 at the rim part 53d is displayed to be shorter than a moving distance L2 at the central part 53b. In other words, when the operation amount is the same, a moving distance with respect to the operation amount is also unchanged, but a display amount with respect to the operation amount varies based on a field curvature.

However, when a ratio of the operation amount and the bending amount is adjusted and the operation amount is the same at the central part 53b, the central part periphery 53c, and the rim part 53d, even if the taken image 70 having a field curvature is displayed as an observation image in the monitor 53a as shown in FIG. 3A, a moving distance with respect to the operation amount is adjusted at the central part 53b, the central part periphery 53c, and the rim part 53d and displayed in the monitor 53a.

Figure 9B:
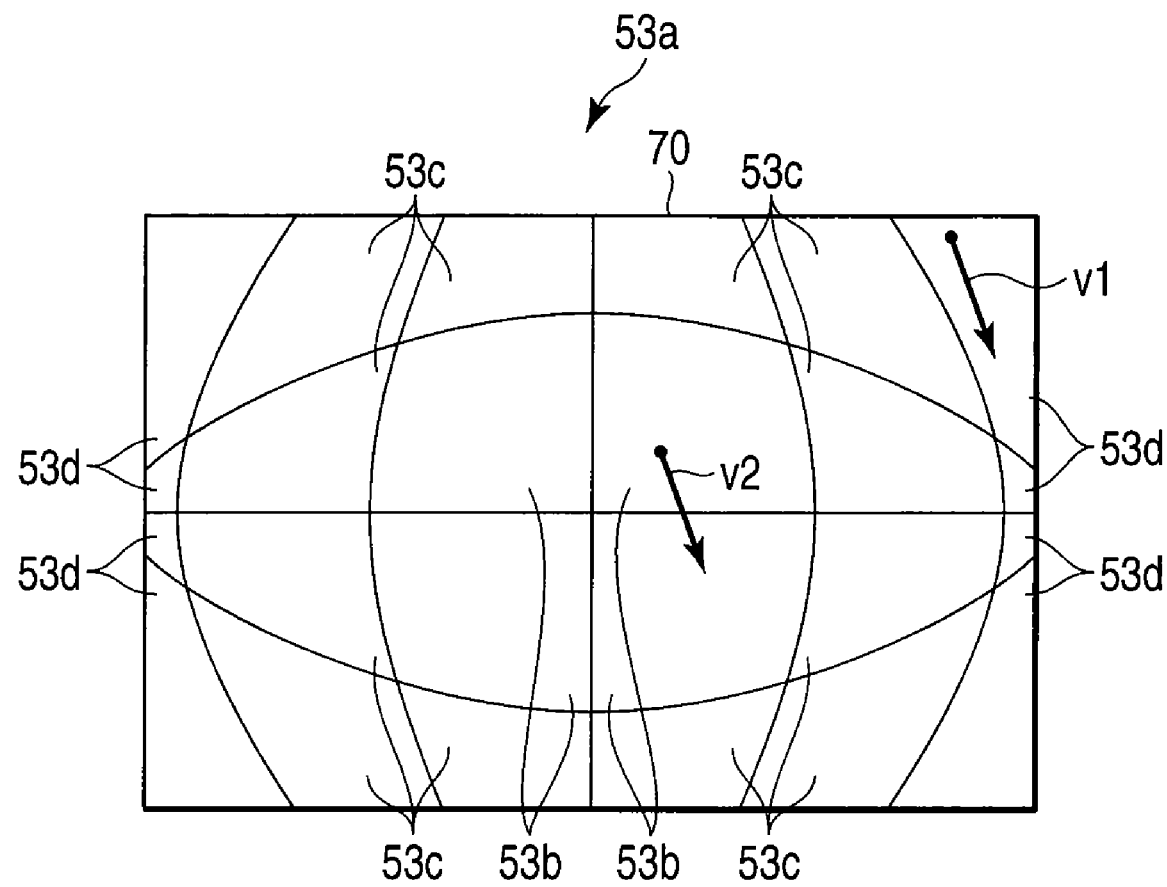
FIG. 9B is a view showing the monitor in which a moving distance at the rim part is displayed to be equal to a moving distance at the central part.

In detail, when the operation amount is the same, performing the adjustment enables reducing a moving distance at, e.g., the rim part 53d to be smaller than a moving distance at the central part 53b. Therefore, when the operation amount is the same, a moving distance is displayed to be the same in the monitor 53a (at the central part 53b, the central part periphery 53c, and the rim part 53d) that displays the taken image 70 having a field curvature. For example, a moving speed v1 at the rim part 53d is observed to be the same as a moving speed v2 at the central part 53b as shown in FIG. 9B. In other words, when the operation amount is the same, a moving distance with respect to the operation amount is adjusted, and a moving speed in the screen with respect to an operation speed remains unchanged based on the field curvature.

It is to be noted that a region in the monitor 53a is previously divided into three regions, i.e., the central part 53b, the central part periphery 53c, and the rim part 53d as shown in FIGS. 3A and 3B. However, the present invention is not restricted thereto, and this number is not limited. These regions can be adjusted in a desired manner by the input device 55. Additionally, a ratio of an operation amount and a bending amount is adjusted by the input device 55 in accordance with the number of the regions.

It is to be noted that the ratio of an operation amount and a bending amount is not restricted to that described above and it can be previously input and set in a desired manner by the input device 55, for example. That is, the input device 55 functions as a setting section that previously sets the ratio of an operation amount and a bending amount in a desired manner.

Figure 10:
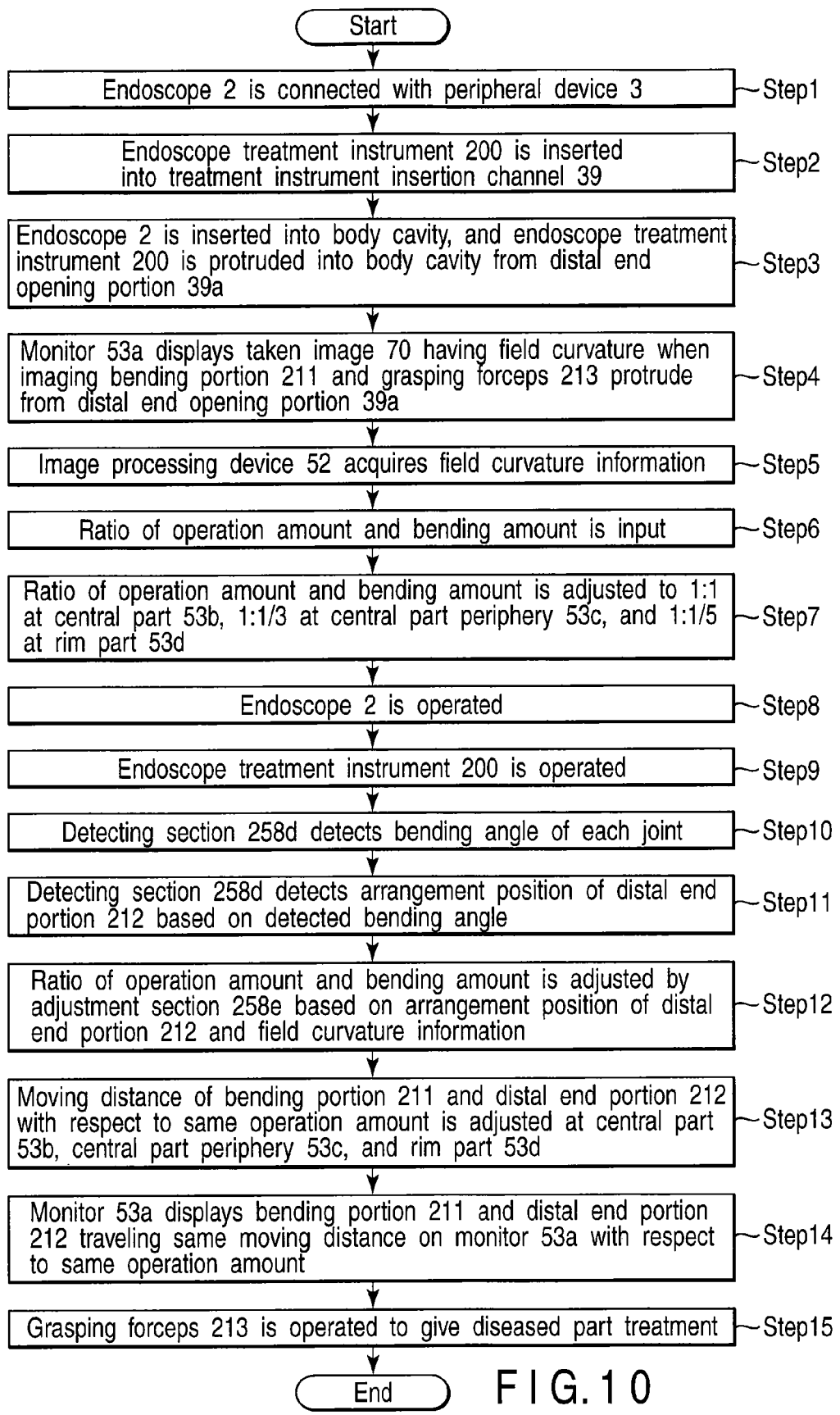
FIG. 10 is a flowchart showing an operation according to a first embodiment.

An operation method in this embodiment will now be explained with reference to a flowchart depicted in FIG. 10.

The endoscope 2 is connected with the peripheral device 3 through the universal cord 33 (Step 1).

The guide tube 50 is connected with the insertion opening 40, and the endoscope treatment instrument 200 is inserted into the treatment instrument insertion channel 39 via the insertion opening 40 from the guide tube 50 (Step 2).

After the endoscope 2 is inserted into a body cavity and the endoscope treatment instrument 200 is operated to be pushed to the distal end hard portion 13 side, the endoscope treatment instrument 200 is protruded (inserted) into the body cavity from the distal end opening portion 39a as shown in FIG. 1 (Step 3).

An imaging range of the imaging section 17 in the body cavity is irradiated with light by the irradiating mechanism 81, e.g., the illumination window 15 and imaged by the imaging mechanism 80, e.g., the observation window 14 or the imaging portion 17. As a result, the taken image 70 of the inside of the body cavity is displayed as an observation image in the monitor 53a as the observing mechanism 83, and the bending portion 211 and the grasping forceps 213 protruding from the distal end opening portion 39a are also displayed in the same way as shown in FIG. 4. That is, as shown in FIG. 4, the monitor 53a displays the taken image 70 having a field curvature obtained when imaging the bending portion 211 and the grasping forceps 213 protruding from the distal end opening portion 39a (Step 4).

Further, when the endoscope 2 is connected with the peripheral device 3 at Step 1, optical characteristics of the optical system 18 are input to the control device 54. The control device 54 identifies field curvature information of the optical system 18 corresponding to the input optical characteristics from combinations stored in the storage section 54a, and outputs the field curvature information to the image processing device 52. The image processing device 52 acquires field curvature information of the taken image 70 that is taken by the imaging section 17 and has a field curvature based on this input field curvature information (Step 5).

It is to be noted that the image processing device 52 may acquire the field curvature information based on the field curvature information input by the input device 55.

The input device 55 inputs the region in the monitor 53a, and the input device 55 adjusts (inputs) a ratio of an operation amount and a bending amount (Step 6). Here, it is assumed that the region in the monitor 53a is divided into three regions, i.e., the central part 53b, the central part periphery 53c, and the rim part 53d as explained above. Furthermore, it is assumed that the ratio of an operation amount and a bending amount in each region is adjusted to 1:1 at the central part 53b, 1:1/3 at the central part periphery 53c, and 1:1/5 at the rim part 53d (Step 7).

It is to be noted that the operations at Steps 6 and 7 may be carried out at any timing between Step 1 and Step 4 or may be preset.

In the state of Step 7, the bending portion 12 is operated by the bending operation knob 32 to be bent in a desired upper, lower, left, or right direction. That is, the endoscope 2 is operated (Step 8).

Then, when the joystick 205 is operated, the driving motor 251, 252, or 253 individually drives in response to the joystick 205. As a result, the operation wires 231, 232, or 233 are pushed or pulled by the swiveling pulley 255, and the node ring 221, 222, or 233 individually independently swivels in the upward, downward, left, or right direction. That is, each joint is curved, thereby bending the bending portion 211.

As explained above, the manipulator (master-slave) type electric endoscope treatment instrument 200 is operated by the joystick 205 in the bending operating section 204 and driven by the driving unit 203 (Step 9).

When the endoscope treatment instrument 200 is driven, the driving motor 251, 252, or 253 drives as explained above. At this time, a signal associated with the number of revolutions of each driving motor is generated by the encoder 251a, 252a, or 253a. The detecting section 258d detects this signal through the motor driver 258b and detects a bending angle of each joint (a swiveling angle in the node ring 221, 222, or 233) from the signal (Step 10).

Moreover, the detecting section 258d detects an arrangement position of the distal end portion 212 based on the detected bending angle (Step 11). It is to be noted that the monitor 53a (the taken image 70) displays the bending portion 211 and the grasping forceps 213 as shown in FIG. 4 or FIGS. 8A, 8B, and 8C. Therefore, the detected arrangement position of the distal end portion 212 is an arrangement position displayed in the monitor 53a.

As a result, the adjustment section 258e adjusts the ratio of an operation amount and a bending amount based on the arrangement position of the distal end portion 212 detected by the detecting section 258d and the field curvature information acquired by the image processing device 52 as the field curvature information acquiring section (Step 12).

For example, when the distal end portion 212 is arranged at the central part 53b as shown in FIG. 8A, the ratio of an operation amount and a bending amount is adjusted to, e.g., 1:1 by the adjustment section 258e.

Additionally, for example, when the distal end portion 212 is arranged at the central part periphery 53c as shown in FIG. 8B, the ratio of an operation amount and a bending amount is adjusted to, e.g., 1:1/3 by the adjustment section 258e.

Further, for example, when the distal end portion 212 is arranged at the rim part 53d as shown in FIG. 8C, the ratio of an operation amount and a bending amount is adjusted to, e.g., 1:1/5 by the adjustment section 258e.

When the ratio of an operation amount and a bending amount is adjusted by the adjustment section 258e, driving of the driving motor 251, 252, or 253 is controlled by the adjustment section 258e. Therefore, at the central part 53b, the central part periphery 53c, and the rim part 53d, a moving distance of the bending portion 211 and the distal end portion 211 with respect to the same operation amount is adjusted (Step 13).

In detail, if the operation amount is the same, for example, a moving distance at the rim part 53d becomes smaller than a moving distance at the central part 53b.

Furthermore, in the monitor 53a, the moving distance of the bending portion 211 and the distal end portion 212 is adjusted and displayed. That is, when the operation amount is the same, a moving distance with respect to the operation amount is adjusted, and a display amount with respect to the operation amount becomes the same based on a field curvature. For example, in the monitor 53a that displays the taken image 70 having a field curvature at the central part 53b, the central part periphery 53c, and the rim part 53d, the bending portion 211 and the distal end portion 212 having the same moving distance in the monitor 53 with respect to the same operation amount are displayed as shown in FIG. 9B (Step 14).

When the treatment instrument operating section 201 is operated in this state, the driving motor 254 drives. As a result, the operation wires 234 are pushed or pulled by the swiveling pulley 255. Therefore, the grasping forceps 213 is operated to give a diseased part a treatment (Step 15), thereby terminating the operation.

It is to be noted that, when the endoscope treatment instrument 200 is again operated by the joystick 205 like Step 9 and driven by the driving motor 251, 252 or 253 after Step 15, the operations at Steps 10 to 14 are repeated. That is, in a state where the endoscope treatment instrument 200 is operated by the joystick 205 and driven by the driving motor 251, 252, or 253, the ratio of an operation amount and a bending amount is constantly adjusted, and driving of the driving motor 251, 252, or 253 is controlled by the adjustment section 258e.

As explained above, according to this embodiment, in the manipulator operation system 1 that remotely operates the endoscope treatment instrument 200 having the articulated mechanism by using the joystick 205, the image processing device 52 acquires field curvature information (Step 5), and the detecting section 258d detects an arrangement position of the distal end portion 212 from the encoders 251a, 252a, and 253a (Step 11). Further, in this embodiment, the ratio of an operation amount and a bending amount is adjusted based on the arrangement position of the distal end portion 212 and the field curvature information (Step 12), a moving distance of the bending portion 211 and the distal end portion 212 with respect to the same operation amount is adjusted (Step 13), and the bending portion 211 and the distal end portion 212 that travel the same moving distance with respect to the same operation amount are displayed in the monitor 53a (Step 14).

As a result, in this embodiment, if the operation amount remains the same, the moving distance of the bending portion 211 and the distal end portion 212 can be adjusted and displayed at any position (e.g., the central part 53b, the central part periphery 53c, and the rim part 53d) on the monitor 53a. That is, according to this embodiment, when the operation amount of the joystick 205 remains the same, adjusting the moving distance of the bending portion 211 and the distal end portion 212 in the monitor 53a (in the observation screen) with respect to this operation amount enables displaying the moving distance of the bending portion 211 and the distal end portion 211 to remain the same at any position in the monitor 53a (enables allowing a display amount to remain the same in the monitor 53a displaying the taken mage 70 having a field curvature).

Therefore, according to the present invention, a sense of discomfort of an operator with respect to an operation can be avoided, the operator does not have to accustom himself/herself to the operation, and a burden of the operation on the operator can be suppressed.

Furthermore, according to this embodiment, even if the bending portion 211 and the distal end portion 212 are moved from, e.g., the central part 53b to the rim part 53d, a moving distance of the bending portion 211 and the distal end portion 212 with respect to an operation amount can be kept the same. Therefore, according to this embodiment, when a diseased part is displayed at, e.g., the rim part 53d, the bending portion 12 does not have to be bent (the endoscope 2 does not have to be operated), and the bending portion 211 and the distal end portion 212 can be readily operated even at the rim part 53d, thus suppressing a burden of the operation on the operator.

Moreover, according to this embodiment, the storage section 54a stores combinations of optical characteristics of the optical system 18 and field curvature information associated with the optical characteristics. Therefore, according to this embodiment, when the endoscope 2 is connected with the peripheral device 3, the field curvature information can be rapidly acquired.

Additionally, according to this embodiment, since the input device 55 can be used to adjust the ratio of an operation amount and a bending amount in a desired manner, the manipulator operation system 1 suitable for the operator can be provided.

It is to be noted that the encoders 251a, 252a, and 253a are used to detect an arrangement position of the distal end portion 212 in this embodiment, but the present invention does not have to be restricted thereto. For example, it is possible to use a potentiometer that measures potential differences before and after driving of the driving motors 251, 252, and 253 or an index such as an LED arranged in the distal end portion 212.

Figure 11:
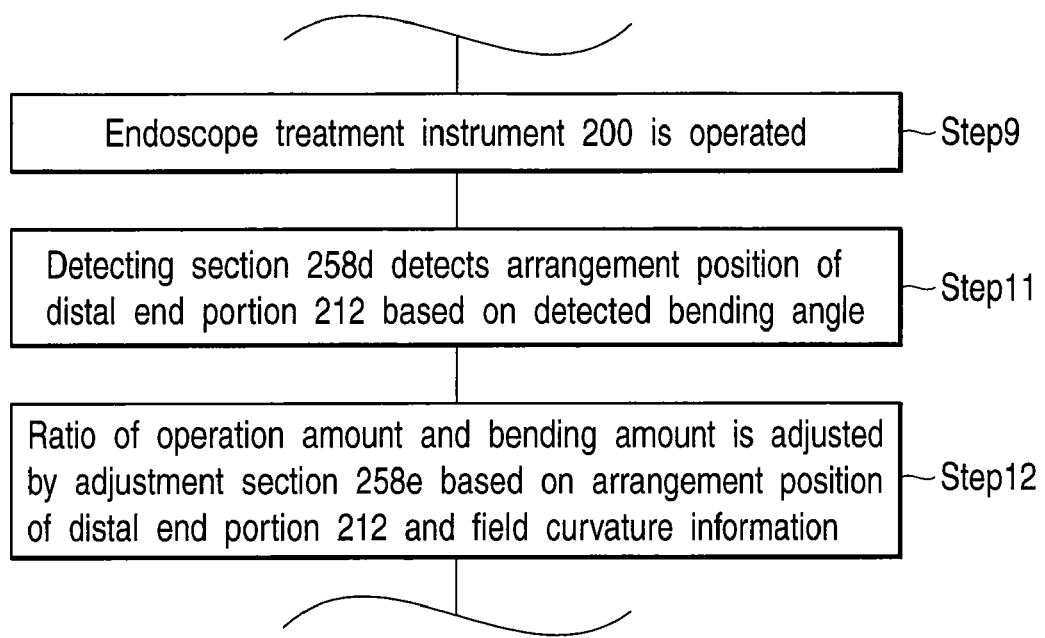
FIG. 11 is a flowchart showing an operation when an index is used.

It is to be noted that, when the index is used, Step 10 is eliminated as shown in FIG. 11. At Step 11, the imaging mechanism 80 serves as a detecting section that detects an arrangement position of the distal end portion 212 based on the index. The arrangement position of the index detected by the imaging mechanism 80 is transmitted to the adjustment section 258e. As a result, Step 12 is carried out.

A second embodiment according to the present invention will now be explained with reference to FIGS. 1, 12, and 13. Like reference numerals denote the same parts as those in the first embodiment, thereby omitting a detailed explanation thereof.

Figure 12:
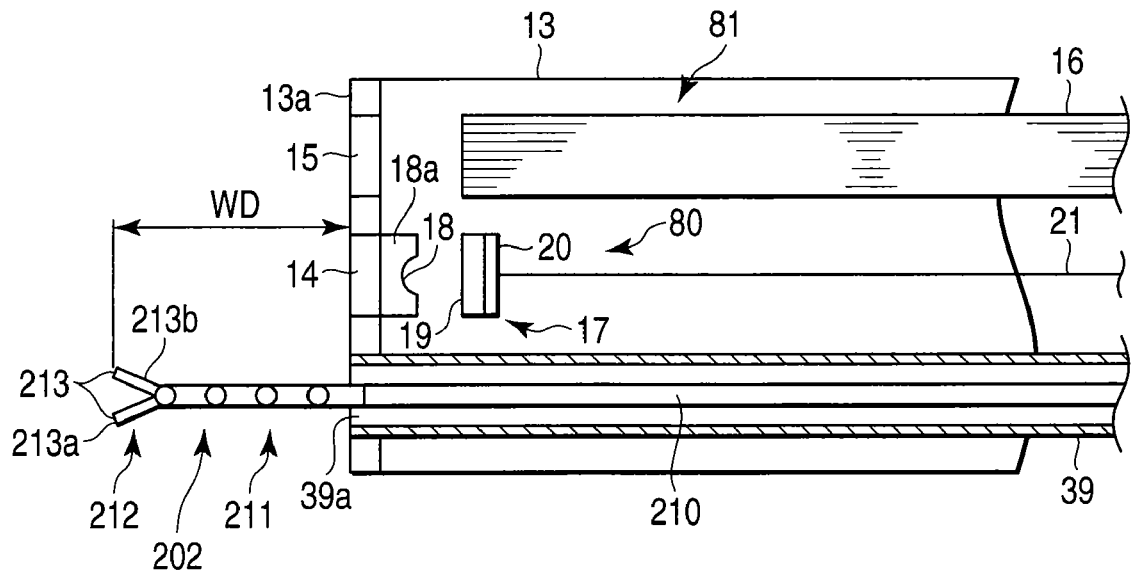
FIG. 12 is a view for explaining a WD in a second embodiment.
Figure 13:
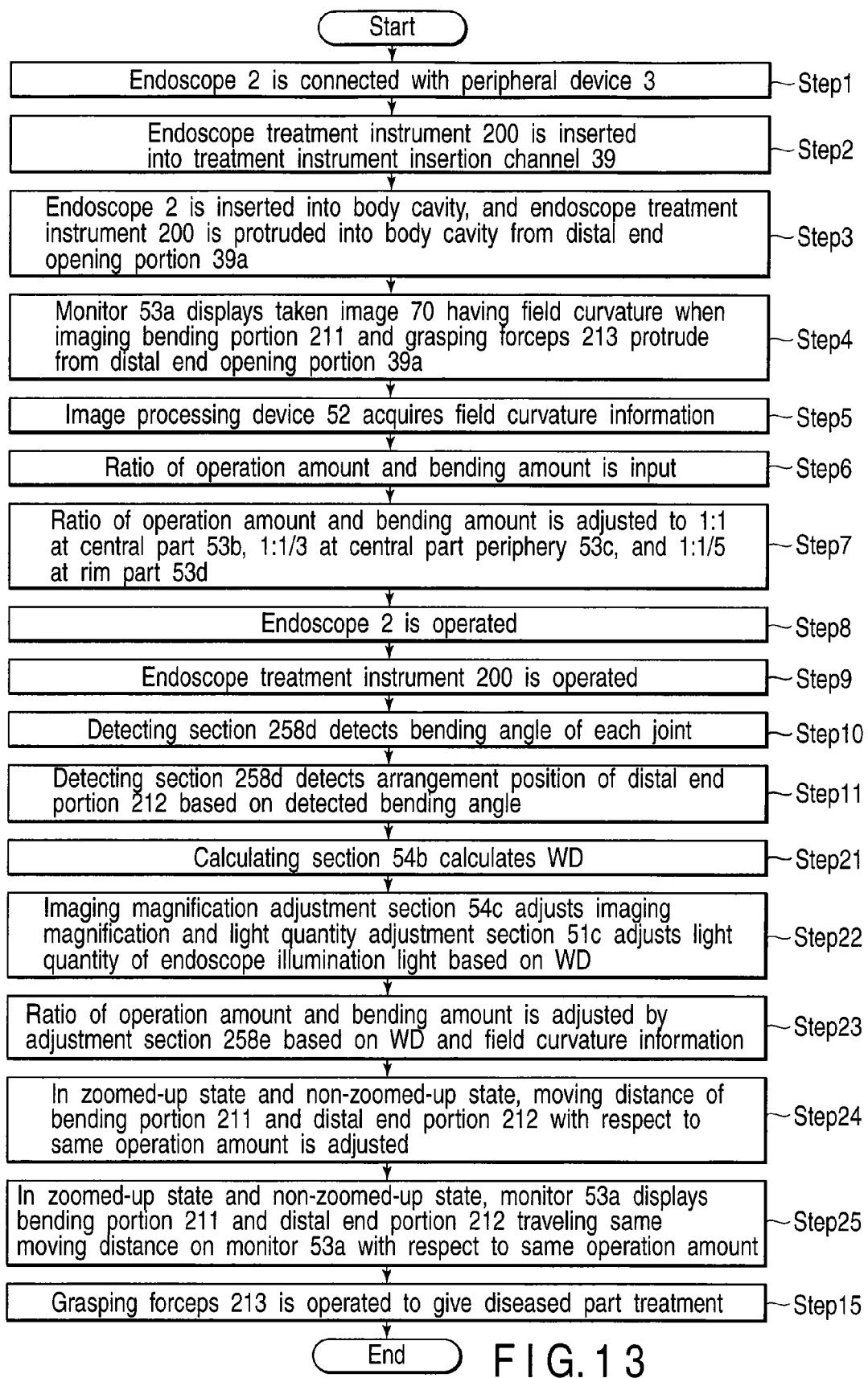
FIG. 13 is a flowchart showing an operation according to the second embodiment.

In this embodiment, a relative distance from a distal end of an endoscope 2 to a distal end of an endoscope treatment instrument 200 protruding from a distal end opening portion 39a as shown in FIG. 12 will be referred to as a working distance (which will be referred to as a WD hereinafter).

It is to be noted that the distal end of the endoscope 2 is an observation window 14 as a distal end of imaging mechanism 80 and it indicates a distal end surface 13a where the observation window 14 is arranged. The distal end of the endoscope treatment instrument 200 indicates a distal end portion 212 (a grasping forceps 213).

In the first embodiment, a moving distance with respect to an operation amount at each of the central part 53b, the central part periphery 53c, and the rim part 53d has been explained. In this embodiment, a moving distance with respect to an operation amount in a zoomed-up observation image and a non-zoomed-up observation image will be explained. A zoomed-up observation image and a non-zoomed-up observation image are displayed in a monitor 53a.

A calculating section 54b that calculates a WD from an arrangement position of the distal end portion 212 detected by a detecting section 258d is provided to a control device 54. The control device 54 serves as calculating mechanism having the calculating section 54b.

The calculating section 54b may be, e.g., a range-finding sensor using endoscope illumination light. The WD is a protrusion amount of a bending portion 211 and the distal end portion 212 protruding from a distal end opening portion 39a. Therefore, the calculating section 54b also serves as a measurement section that measures a protrusion amount.

Additionally, the control device 54 according to this embodiment has an imaging magnification adjustment section 54c that adjusts an imaging magnification of an imaging section 17 in accordance with a WD calculated by the calculating section 54b. The control device 54 is imaging magnification adjusting mechanism having the imaging magnification adjustment section 54c.

The imaging magnification adjustment section 54c moves an object lens 18a in an axial direction in accordance with a WD to adjust an imaging magnification. As a result, a display magnification in the monitor 53a is adjusted. Therefore, the monitor 53a displays an observation image in a zoomed-up state or an observation image in a non-zoomed-up state. The zoomed-up state means a state where a WD is, e.g., less than 25 mm, and the non-zoomed-up state means a state where a WD is, e.g., 25 mm or above.

Further, to a light source device 51 according to this embodiment is provided a light quantity adjustment section 51c that adjusts a light quantity of endoscope illumination light that is generated by the light source device 51 and applied to an imaging range of the imaging section 17 by an illumination window 15 as an irradiating section. The light source device 51 functions as light quantity adjusting mechanism having the light quantity adjustment section 51c.

It is to be noted that the light quantity adjustment section 51c may adjust a light quantity of endoscope illumination light based on the imaging magnification adjusted by the imaging magnification adjustment section 54c in accordance with the WD.

When the WD is, e.g., less than 15 mm, the imaging magnification adjustment section 54c does not change the imaging magnification (e.g., one magnification) and the light quantity adjustment section 51c does not change the light quantity of the endoscope illumination light, for example.

When the WD is, e.g., 15 mm or above and less than 25 mm, the imaging magnification adjustment section 54c adjusts the imaging magnification to, e.g., a minimum magnification (e.g., 1.2 magnification) and the light quantity adjustment section 51c adjusts the light quantity of the endoscope illumination light to, e.g., a minimum value.

When the WD is, e.g., 25 mm or above and less than 35 mm, the imaging magnification adjustment section 54c adjusts the imaging magnification to, e.g., an intermediate magnification (e.g., 1.4 magnification) and the light quantity adjustment section 51c adjusts the light quantity of the endoscope illumination light to, e.g., an intermediate value.

When the WD is, e.g., 35 mm or above, the imaging magnification adjustment section 54c adjusts the imaging magnification to, e.g., a maximum magnification (e.g., 1.6 magnification) and the light quantity adjustment section 51c adjusts the light quantity of the endoscope illumination light to, e.g., a maximum value.

The detecting section 258d in this embodiment detects an arrangement position of the distal end portion 212 like the first embodiment. It is to be noted that the detecting section 258d is included in a treatment instrument distal end movement control device 300.

An adjustment section 258e adjusts a ratio of an operation amount and a bending amount based on the WD (a protrusion amount) calculated by the calculating section 54b and field curvature information acquired by an image processing device 52 as a field curvature information acquiring section to control a driving unit 203. It is to be noted that the adjustment section 258e in this embodiment may further adjust the ratio of an operation amount and a bending amount based on the imaging magnification adjusted by the imaging magnification adjustment section 54c.

When the WD is calculated as, e.g., a value less than 15 mm by the calculating section 54b and the field curvature information is acquired by the image processing device 52, the adjustment section 258e adjusts the ratio of an operation amount and a bending amount to, e.g., 1:1 to control the driving unit 203 (driving motors 251, 252, and 253).

When the WD is calculated as, e.g., a value that is 15 mm or above and less than 25 mm by the calculating section 54b and the field curvature information is acquired by the image processing device 52, the adjustment section 258e adjusts the ratio of an operation amount and a bending amount to, e.g., 1:1/2 to control the driving unit 203.

When the WD is calculated as, e.g., a value that is 25 mm or above and less than 35 mm by the calculating section 54b and the field curvature information is acquired by the image processing device 52, the adjustment section 258e adjusts the ratio of an operation amount and a bending amount to, e.g., 1:1/3 to control the driving unit 203.

When the WD is calculated as, e.g., a value equal to or above 35 mm by the calculating section 54b and the field curvature information is acquired by the image processing device 52, the adjustment section 258e adjusts the ratio of an operation amount and a bending amount to, e.g., 1:1/4 to control the driving unit 203.

When the ratio of an operation amount and a bending amount is adjusted as explained above and an operation amount remains the same, even if a taken image 70 having a field curvature is displayed as a zoomed-up observation image or a non-zoomed-up observation image in the monitor 53a, a moving distance with respect to the operation amount is adjusted and displayed in the monitor 53a.

In detail, for example, when the operation amount remains the same, a moving distance in, e.g., the non-zoomed-up observation image becomes smaller than a moving distance in the zoomed-up observation image by the adjustment. Therefore, when the operation amount remains the same, a moving distance is displayed to remain the same in the monitor 53a displaying the zoomed-up observation image or the non-zoomed-up observation image (the taken image 70 having a field curvature). For example, a moving distance in the zoomed-up observation image is displayed to be equal to a moving distance in the non-zoomed-up observation image. In other words, when the operation amount remains the same, a moving distance with respect to the operation amount is adjusted, and a display amount with respect to the operation amount remains the same due to the field curvature in the zoomed-up state and the non-zoomed-up state.

It is to be noted that the WD is previously classified into four ranges, i.e., less than 15 mm, 15 mm or above and less than 25 mm, 25 mm or above and less than 35 mm, and 35 mm or above. However, the present invention does not have to be restricted thereto, and these ranges and values in these ranges are not limited. These ranges and values in these ranges can be adjusted in a desired manner by an input device 55. Further, the ratio of an operation amount and a bending amount is adjusted by the input device 55 in accordance with the number of regions. It is to be noted that the imaging magnification adjusted by the imaging magnification adjustment section 54c and the light quantity of the endoscope illumination light adjusted by the light quantity adjustment section 51c may be adjusted by the input device 55 based on the number of the regions or numeral values.

It is to be noted that the ratio of an operation amount and a bending amount is not restricted to the above description and it can be input by, e.g., the input device 55 to be adjusted in a desired manner as explained above. That is, the input device 55 serves as an input section that adjustably inputs the ratio of an operation amount and a bending amount, the ranges and values in the ranges, the imaging magnification, or the light quantity in a desired manner.

An operation method in this embodiment will now be explained with reference to a flowchart depicted in FIG. 13.

Operations from Step 1 to Step 11 are the same as those in the first embodiment, thereby omitting an explanation thereof.

The calculating section 54b calculates a WD (Step 21).

Based on the WD calculated by the calculating section 54b, the imaging magnification adjustment section 54c adjusts an imaging magnification, and the light quantity adjustment section 51c adjusts a light quantity of endoscope illumination light (Step 22).

It is to be noted that the light quantity adjustment section 51c may adjust the light quantity of the endoscope illumination light based on the imaging magnification at Step 22 as explained above.

When the WD is, e.g., less than 15 mm at Step 21, the imaging magnification is not changed and the light quantity of the endoscope illumination light is not changed either at Step 22, for example.

When the WD is, e.g., 15 mm or above and less than 25 mm at Step 21, the imaging magnification is adjusted to, e.g., a minimum magnification and the light quantity of the endoscope illumination light is adjusted to, e.g., a minimum value at Step 22.

When the WD is, e.g., 25 mm or above and less than 35 mm at Step 21, the imaging magnification is adjusted to, e.g., an intermediate magnification and the light quantity of the endoscope illumination light is adjusted to, e.g., an intermediate value at Step 22.

When the WD is, e.g., 35 mm at Step 21, the imaging magnification is adjusted to, e.g., a maximum magnification and the light quantity of the endoscope illumination light is adjusted to, e.g., a maximum value at Step 22.

In this manner, a display magnification is adjusted in accordance with the WD, and a zoomed-up observation image or a non-zoomed-up observation image is displayed in the monitor 53a.

Then, a ratio of an operation amount and a bending amount is adjusted by the adjustment section 258e based on the WD calculated by the calculating section 54b and field curvature information acquired by the image processing device 52 as the field curvature information acquiring section (Step 23).

When the WD is, e.g., less than 15 mm at Step 21, the ratio of an operation amount and a bending amount is adjusted to, e.g., 1:1 by the adjustment section 258e at Step 23.

When the WD is, e.g., 15 m or above and less than 25 mm at Step 21, the ratio of an operation amount and a bending amount is adjusted to, e.g., 1:1/2 by the adjustment section 258e at Step 23.

When the WD is, e.g., 25 mm or above and less than 35 mm at Step 21, the ratio of an operation amount and a bending amount is adjusted to, e.g., 1:1/3 by the adjustment section 258e at Step 23.

When the WD is, e.g., 35 mm or above at Step 21, the ratio of an operation amount and a bending amount is adjusted to, e.g., 1:1/4 by the adjustment section 258e at Step 23.

In this embodiment, the ratio of an operation amount and a bending amount is adjusted based on a protrusion amount as the WD at Step 23.

It is to be noted that the imaging magnification adjusted by the imaging magnification adjustment section 54c at Step 22 may be further used to adjust the ratio of an operation amount and a bending amount at Step 23.

When the ratio of an operation amount and a bending amount is adjusted by the adjustment section 258e at Step 23, the driving motor 251, 252, or 253 is controlled by the adjustment section 258e. Therefore, the moving distance of the bending portion 211 and the distal end portion 212 with respect to the same operation amount is adjusted in the zoomed-up state and the non-zoomed-up state (Step 24).

In detail, if the operation amount remains the same, the moving distance in, e.g., the non-zoomed-up observation image becomes smaller than the moving distance in the zoomed-up observation image.

Further, the moving distance of the bending portion 211 and the distal end portion 212 is adjusted and displayed in the monitor 53a. That is, if the operation amount remains the same, the moving distance with respect to the operation amount is adjusted, and a display amount with respect to the operation amount remains the same due to the field curvature. For example, in the zoomed-up state and the non-zoomed-up state, the monitor 53a displaying the taken image 70 having the field curvature displays the bending portion 211 and the distal end portion 212 that travel the same moving distance in the monitor 53a with respect to the same operation amount (Step 25).

After Step 25, an operation at Step 15 is carried out.

It is to be noted that, after Step 15, when the endoscope treatment instrument 200 is again operated by the joystick 205 like Step 9 and the driving motor 251, 252, or 253 is used to perform driving, the operations at Steps 10 and 11 and Steps 21 to 25 are repeated. That is, in a state where the endoscope treatment instrument 200 is operated by the joystick 205 and a WD is changed, the WD is constantly calculated, an imaging magnification is adjusted, a ratio of an operation amount and a bending amount is adjusted, and the driving motor 251, 252, or 253 is controlled by the adjustment section 258e.

As explained above, according to this embodiment, the image processing device 52 acquires field curvature information (Step 5), and the detecting section 258d detects an arrangement position of the distal end portion 212 from encoders 251a, 252a, and 253a (Step 11). Then, in this embodiment, the calculating section 54b calculates a WD from the arrangement position of the distal end portion 212 (Step 21), the imaging magnification adjustment section 54c adjusts an imaging magnification of the imaging section 17 in accordance with the WD, and the monitor 53a displays a zoomed-up image and a non-zoomed-up image in accordance with the WD (Step 22). Moreover, in this embodiment, the light quantity adjustment section 51c adjusts a light quantity of endoscope illumination light in accordance with the WD (Step 22). Additionally, in this embodiment, a ratio of an operation amount and a bending amount is adjusted based on the WD and the field curvature information (Step 23), and a moving distance of the bending portion 211 and the distal end portion 212 with respect to the same operation amount is adjusted in the zoomed-up state and the non-zoomed-up state (Step 24). Further, according to this embodiment, in the zoomed-up state and the non-zoomed-up state, the bending portion 211 and the distal end portion 212 that travel the same moving distance in the monitor 53a with respect to the same operation amount are displayed (Step 25).

As a result, according to this embodiment, in the monitor 53a that displays a zoomed-up image and a non-zoomed-up image in accordance with the WD, if the operation amount remains the same, the moving distance of the bending portion 211 and the distal end portion 212 can be adjusted and displayed like the first embodiment. Therefore, according to this embodiment, in both the zoomed-up image and the non-zoomed-up image, a sense of discomfort of an operator with respect to an operation can be avoided, the operator does not have to accustom himself/herself to the operation, and a burden of the operation on the operator can be suppressed.

Furthermore, according to this embodiment, since the imaging magnification can be adjusted in accordance with the WD without bending the bending portion 12 (operating the endoscope 2) like the first embodiment, the monitor 53a can display both the zoomed-up image and the non-zoomed-up image. Moreover, according to this embodiment, a light quantity of endoscope illumination light can be adjusted at the same time, and the moving distance with respect to the operation amount can be adjusted. Therefore, according to this embodiment, even in a state where the zoomed-up image and the non-zoomed-up image are displayed, if the operation amount remains the same, the moving distance is displayed to remain unchanged in the monitor, a sense of discomfort of the operator with respect to the operation can be avoided, the operator does not have to accustom himself/herself to the operation, and a burden of the operation on the operator can be suppressed.

Additionally, according to this embodiment, the input device 55 can adjust the ranges of the WD and values in the ranges, the imaging magnification, the light quantity of the endoscope illumination light, and the ratio of an operation amount and a bending amount. Therefore, this embodiment can provide the manipulator operation system 1 conforming to a view field angle of the endoscope or an operator.

It is to be noted that the bending portion 211 and the distal end portion 212 are protruded from the distal end opening portion 39a in the manipulator operation system 1 according to this embodiment but the present invention does not have to be restricted thereto.

Figure 14A:
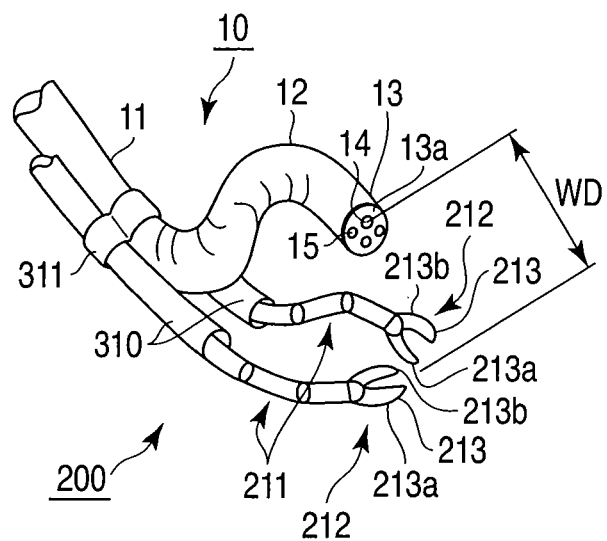
FIG. 14A is a schematic view showing another conformation of the manipulator operation system.

For example, in the manipulator operation system 1 depicted in FIG. 14A, the endoscope treatment instrument 200 is inserted into an external channel 310 arranged outside an inserting portion 10 without being inserted into the endoscope 2 (a treatment instrument insertion channel 39), and the bending portion 211 and the distal end portion 212 are protruded from the external channel 310. The external channel 310 is fixed to a flexible tube portion 11 by a fixture 311.

Figure 14B:
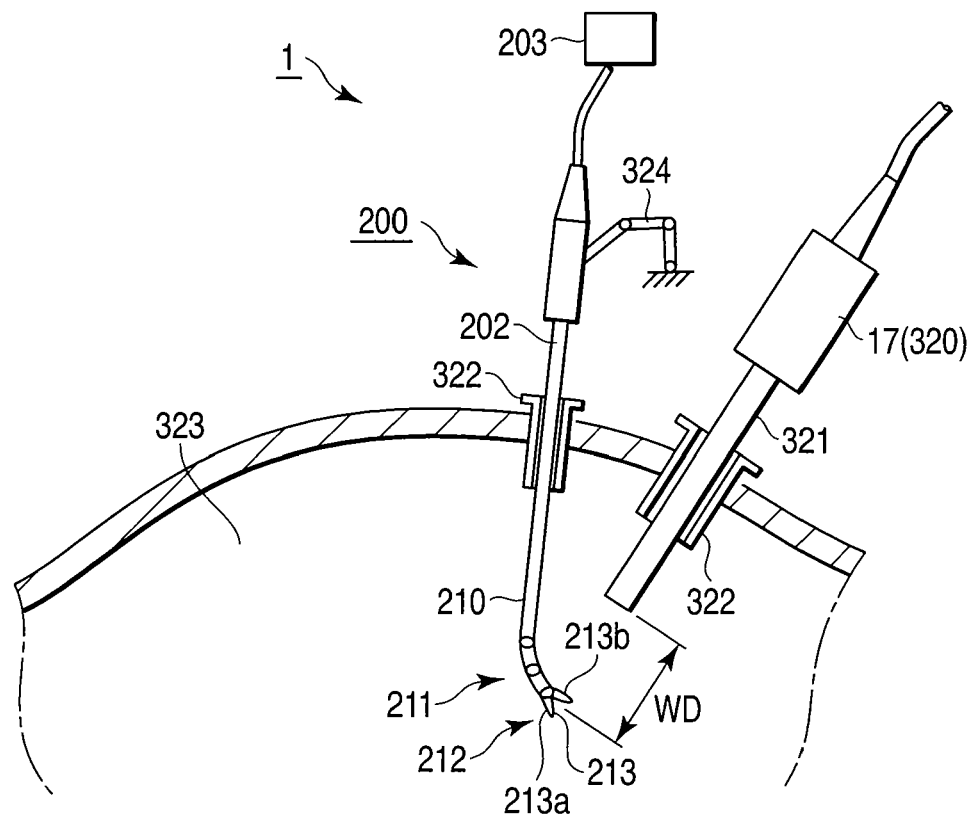
FIG. 14B is a schematic view showing another conformation of the manipulator operation system.

Furthermore, in the manipulator operation system 1 depicted in FIG. 14B, the endoscope treatment instrument 200 having a hard inserting portion 202 and a hard mirror 321 having a TV camera 320 as the imaging section 17 are inserted into a body cavity 323 through different trocars 322. The endoscope treatment instrument 200 is supported at an intermediate end by a support portion 324 and connected with the driving unit 203 at a proximal end. Although not shown, the hard mirror 321 is connected with a peripheral device 3 like the foregoing embodiment.

As explained above, in this embodiment, the bending portion 211 and the distal end portion 212 may not be protruded from the distal end opening portion 39a that is provided on the same plane with the observation window 14, and the imaging section 17, the bending portion 211, and the distal end portion 212 may be configured as separate members. That is, in this embodiment, even if the distal end opening portion 39a as a protrusion opening for the bending portion 211 and the distal end portion 212 is not arranged on the same plane as the observation window 14 included in the imaging mechanism 80 as shown in, e.g., FIG. 1, the calculating section 54b can calculate a WD. Therefore, this embodiment can obtain the above-explained effect and can be used for various types of manipulator operation system 1.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A manipulator operation system comprising:
 a treatment instrument distal end movement control section having: an endoscope treatment instrument having a bending portion bendable in a desired direction and a distal end portion that is directly or indirectly coupled with the bending portion and has a treatment instrument that gives a diseased part a treatment; a bending driving section that drives the bending portion to bend; and a bending operating section that operates the bending driving section to bend the bending portion;
 imaging mechanism having an imaging section that includes an optical system having a field curvature, images the distal end portion and the bending portion by using the optical system, and provided separately from the endoscope treatment instrument;
 observing mechanism having a display section that displays as an observation image a taken image that is taken by the imaging section and has the field curvature;
 detecting mechanism having a detecting section that detects an arrangement position of the distal end portion that is imaged by the imaging section to be displayed in the display section;

field curvature information acquiring mechanism having a field curvature information acquiring section that acquires field curvature information of the taken image; and adjusting mechanism having an adjustment section that adjusts a ratio of an operation amount of the bending operating section and a driving amount of the bending driving section based on the arrangement position detected by the detecting section and the field curvature information acquired by the field curvature information acquiring section.

2. The system according to claim 1, having an input section that inputs field curvature information of the optical system, wherein the field curvature information acquiring section acquires the field curvature information of the taken image based on the field curvature information of the optical system input from the input section.

3. The system according to claim 1, wherein the field curvature information acquiring section acquires the field curvature information of the taken image based on the field curvature information of the optical system when the imaging mechanism is connected with the field curvature information acquiring mechanism.

4. The system according to claim 1, having a setting section that previously sets the ratio of the operation amount and the driving amount adjusted by the adjustment section.

5. A manipulator operation system comprising:
a treatment instrument distal end movement control section having: an endoscope treatment instrument having a bending portion bendable in a desired direction and a distal end portion that is directly or indirectly coupled with the bending portion and has a treatment instrument that gives a diseased part a treatment; a bending driving section that drives the bending portion to bend; a bending operating section that operates the bending driving section to bend the bending portion; and a detecting section that detects an arrangement position of the distal end portion;
imaging mechanism having an imaging section that includes an optical system having a field curvature, images the distal end portion and the bending portion by using the optical system, and provided separately from the endoscope treatment instrument;
calculating mechanism having a calculating section that calculates a relative distance from a distal end of the imaging section to the distal end portion from the arrangement position detected by the detecting section;
observing mechanism having a display section that displays as an observation image a taken image that is taken by the imaging section and has the field curvature;
field curvature information acquiring mechanism having a field curvature information acquiring section that acquires field curvature information of the taken image; and
adjusting mechanism having an adjustment section that adjusts a ratio of an operation amount of the bending operating section and a driving amount of the bending driving section based on the relative distance calculated by the calculating section and the field curvature information acquired by the field curvature information acquiring section.

6. The system according to claim 5, further having an endoscope that has a distal end opening portion of an insertion channel in which the endoscope treatment instrument is inserted and an observation window that is arranged on the same plane as the distal end opening portion and included in the imaging mechanism in the distal end portion,
wherein the calculating section also serves as a measurement section that measures a protrusion amount of the bending portion and the distal end portion protruding from the distal end opening portion, and
the adjustment section adjusts the ratio based on the protrusion amount.

7. The system according to claim 6, having an input section that inputs field curvature information of the optical system, wherein the field curvature information acquiring section acquires the field curvature information of the taken image based on the field curvature information of the optical system input from the input section.

8. The system according to claim 6, wherein the field curvature information acquiring section acquires the field curvature information of the taken image based on the field curvature information of the optical system when the imaging mechanism is connected with the field curvature information acquiring mechanism.

9. The system according to claim 6, having a setting section that previously sets the ratio of the operation amount and the driving amount adjusted by the adjustment section.

10. The system according to claim 5, having imaging magnification adjusting mechanism including an imaging magnification adjustment section that adjusts an imaging magnification of the imaging section in accordance with the relative distance calculated by the calculating section,
wherein the adjustment section further adjusts the ratio based on the imaging magnification.

11. The system according to claim 10, further having:
an irradiating section that irradiates an imaging range of the imaging section with illumination light; and
light quantity adjusting mechanism including a light quantity adjustment section that adjusts a light quantity of the illumination light applied by the irradiating section in accordance with the relative distance calculated by the calculating section.

12. The system according to claim 10, further having:
an irradiating section that irradiates an imaging range of the imaging section with illumination light; and
light quantity adjusting mechanism including a light quantity adjustment section that adjusts a light quantity of the illumination light applied by the irradiating section in accordance with the imaging magnification calculated by the imaging magnification adjustment section.

13. The system according to claim 10, having an input section that inputs field curvature information of the optical system,
wherein the field curvature information acquiring section acquires the field curvature information of the taken image based on the field curvature information of the optical system input from the input section.

14. The system according to claim 10, wherein the field curvature information acquiring section acquires the field curvature information of the taken image based on the field curvature information of the optical system when the imaging mechanism is connected with the field curvature information acquiring mechanism.

15. The system according to claim 10, having a setting section that previously sets the ratio of the operation amount and the driving amount adjusted by the adjustment section.

16. The system according to claim 5, having an input section that inputs field curvature information of the optical system,
wherein the field curvature information acquiring section acquires the field curvature information of the taken image based on the field curvature information of the optical system input from the input section.

17. The system according to claim 5, wherein the field curvature information acquiring section acquires the field curvature information of the taken image based on the field curvature information of the optical system when the imaging mechanism is connected with the field curvature information acquiring mechanism.

18. The system according to claim 5, having a setting section that previously sets the ratio of the operation amount and the driving amount adjusted by the adjustment section.

* * * * *